(12) United States Patent
Sun et al.

(10) Patent No.: US 9,788,933 B2
(45) Date of Patent: Oct. 17, 2017

(54) MEDICAL DEVICE DELIVERY SYSTEM AND DEPLOYMENT METHOD

(75) Inventors: Jichao Sun, West Lafayette, IN (US); Jarin Kratzberg, Lafayette, IN (US); David D. Grewe, West Lafayette, IN (US); Kenneth Haselby, Battle Ground, IN (US); Matthew S. Huser, West Lafayette, IN (US); Steven J. Charlebois, West Lafayette, IN (US); William Kurt Dierking, Louisville, KY (US); Alan R. Leewood, Lafayette, IN (US); Brandt M. Davis, Palm Beach Gardens, FL (US); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 308 days.

(21) Appl. No.: 13/881,632

(22) PCT Filed: Oct. 28, 2011

(86) PCT No.: PCT/US2011/058370
§ 371 (c)(1),
(2), (4) Date: Apr. 25, 2013

(87) PCT Pub. No.: WO2012/058582
PCT Pub. Date: May 3, 2012

(65) Prior Publication Data
US 2013/0218257 A1    Aug. 22, 2013

Related U.S. Application Data

(60) Provisional application No. 61/408,145, filed on Oct. 29, 2010.

(51) Int. Cl.
*A61F 2/07* (2013.01)
*A61F 2/06* (2013.01)
(Continued)

(52) U.S. Cl.
CPC ............. *A61F 2/07* (2013.01); *A61F 2/064* (2013.01); *A61F 2/848* (2013.01); *A61F 2/89* (2013.01);
(Continued)

(58) Field of Classification Search
CPC ............. A61F 2002/061; A61F 2/856; A61F 2002/8483; A61F 2002/8486
(Continued)

(56) References Cited

U.S. PATENT DOCUMENTS 5,397,355 A     3/1995  Marin et al.
5,421,955 A *   6/1995  Lau .................. A61F 2/88
                                            216/48

(Continued)

FOREIGN PATENT DOCUMENTS

| WO | WO2004/002371 | 1/2004 |
| WO | WO2008/057568 | 5/2008 |
| WO | WO2012/006146 | 1/2012 |

OTHER PUBLICATIONS

International Search Report and Written Opinion for PCT/US2011/058370 mailed Feb. 17, 2012, 13 pgs.

*Primary Examiner* — Thomas J Sweet
*Assistant Examiner* — Cheryl Miller
(74) *Attorney, Agent, or Firm* — Brinks Gilson & Lione

(57) ABSTRACT

An aortic stent-graft may include a tubular graft extending from a proximal end to a distal end, the graft comprising a proximal sealing portion and an intermediate portion, wherein a proximal end of the intermediate portion abuts the distal end of the proximal sealing portion. At least one sealing stent may be attached to the proximal sealing portion. A first fenestration window is disposed in the intermediate portion. The first fenestration window has a length determined by the equation L=1.23*D−24 millimeters, (Continued)

where L is the length of the first fenestration window. D is between about 24 millimeters and 45 millimeters.

16 Claims, 15 Drawing Sheets

(51) Int. Cl.
　　*A61F 2/82*　　　(2013.01)
　　*A61F 2/848*　　 (2013.01)
　　*A61F 2/89*　　　(2013.01)
　　*A61F 2/915*　　 (2013.01)
(52) U.S. Cl.
　　CPC ......... *A61F 2/915* (2013.01); *A61F 2002/061* (2013.01); *A61F 2002/065* (2013.01); *A61F 2002/067* (2013.01); *A61F 2002/075* (2013.01); *A61F 2002/826* (2013.01); *A61F 2002/8483* (2013.01); *A61F 2220/005* (2013.01); *A61F 2220/0016* (2013.01); *A61F 2220/0075* (2013.01); *A61F 2230/0078* (2013.01); *A61F 2250/006* (2013.01); *A61F 2250/0018* (2013.01); *A61F 2250/0023* (2013.01); *A61F 2250/0039* (2013.01); *A61F 2250/0071* (2013.01); *A61F 2250/0098* (2013.01)
(58) Field of Classification Search
　　USPC .............................. 623/1.14, 1.36, 1.35, 1.16
　　See application file for complete search history.

(56) References Cited

U.S. PATENT DOCUMENTS

| | | | |
|---|---|---|---|
| 5,591,197 A | 1/1997 | Orth et al. | |
| 5,617,878 A | 4/1997 | Taheri | |
| 5,720,776 A * | 2/1998 | Chuter et al. | 623/1.36 |
| 5,749,918 A | 5/1998 | Hogendijk et al. | |
| 5,843,164 A | 12/1998 | Frantzen et al. | |
| 6,090,127 A * | 7/2000 | Globerman | A61F 2/90 606/194 |
| 6,113,612 A | 9/2000 | Swanson et al. | |
| 6,231,581 B1 * | 5/2001 | Shank et al. | 606/157 |
| 6,702,844 B1 | 3/2004 | Lazarus | |
| 7,044,962 B2 | 5/2006 | Elliott | |
| 7,144,421 B2 | 12/2006 | Carpenter et al. | |
| 7,220,274 B1 * | 5/2007 | Quinn | A61F 2/07 623/1.13 |
| 2002/0107561 A1 * | 8/2002 | Pinheiro | 623/1.14 |
| 2002/0198585 A1 * | 12/2002 | Wisselink | A61F 2/07 623/1.11 |
| 2003/0135257 A1 * | 7/2003 | Taheri | A61B 17/00234 623/1.11 |
| 2004/0260382 A1 | 12/2004 | Fogarty et al. | |
| 2005/0131518 A1 * | 6/2005 | Hartley et al. | 623/1.13 |
| 2006/0161241 A1 * | 7/2006 | Barbut | A61F 2/013 623/1.15 |
| 2006/0247761 A1 * | 11/2006 | Greenberg | A61F 2/07 623/1.16 |
| 2007/0233227 A1 | 10/2007 | Greenan | |
| 2007/0233229 A1 * | 10/2007 | Berra | A61F 2/07 623/1.13 |
| 2008/0039922 A1 | 2/2008 | Miles et al. | |
| 2008/0097578 A1 * | 4/2008 | Erickson | A61F 2/07 623/1.16 |
| 2008/0114446 A1 * | 5/2008 | Hartley | A61F 2/07 623/1.13 |
| 2009/0043371 A1 * | 2/2009 | Fearnot | A61F 2/07 623/1.13 |
| 2009/0048663 A1 * | 2/2009 | Greenberg | A61F 2/07 623/1.35 |
| 2009/0093873 A1 * | 4/2009 | Navia | 623/1.23 |
| 2009/0240316 A1 | 9/2009 | Bruszewski | |
| 2009/0254172 A1 * | 10/2009 | Grewe | 623/1.15 |
| 2009/0259290 A1 | 10/2009 | Bruszewski et al. | |
| 2010/0057195 A1 * | 3/2010 | Roeder et al. | 623/1.35 |
| 2010/0249899 A1 * | 9/2010 | Chuter et al. | 623/1.13 |
| 2010/0268318 A1 * | 10/2010 | Glynn | A61F 2/07 623/1.13 |
| 2010/0292772 A1 * | 11/2010 | Samuels | A61F 2/07 623/1.11 |
| 2012/0323303 A1 * | 12/2012 | Ivancev | A61F 2/07 623/1.13 |

* cited by examiner

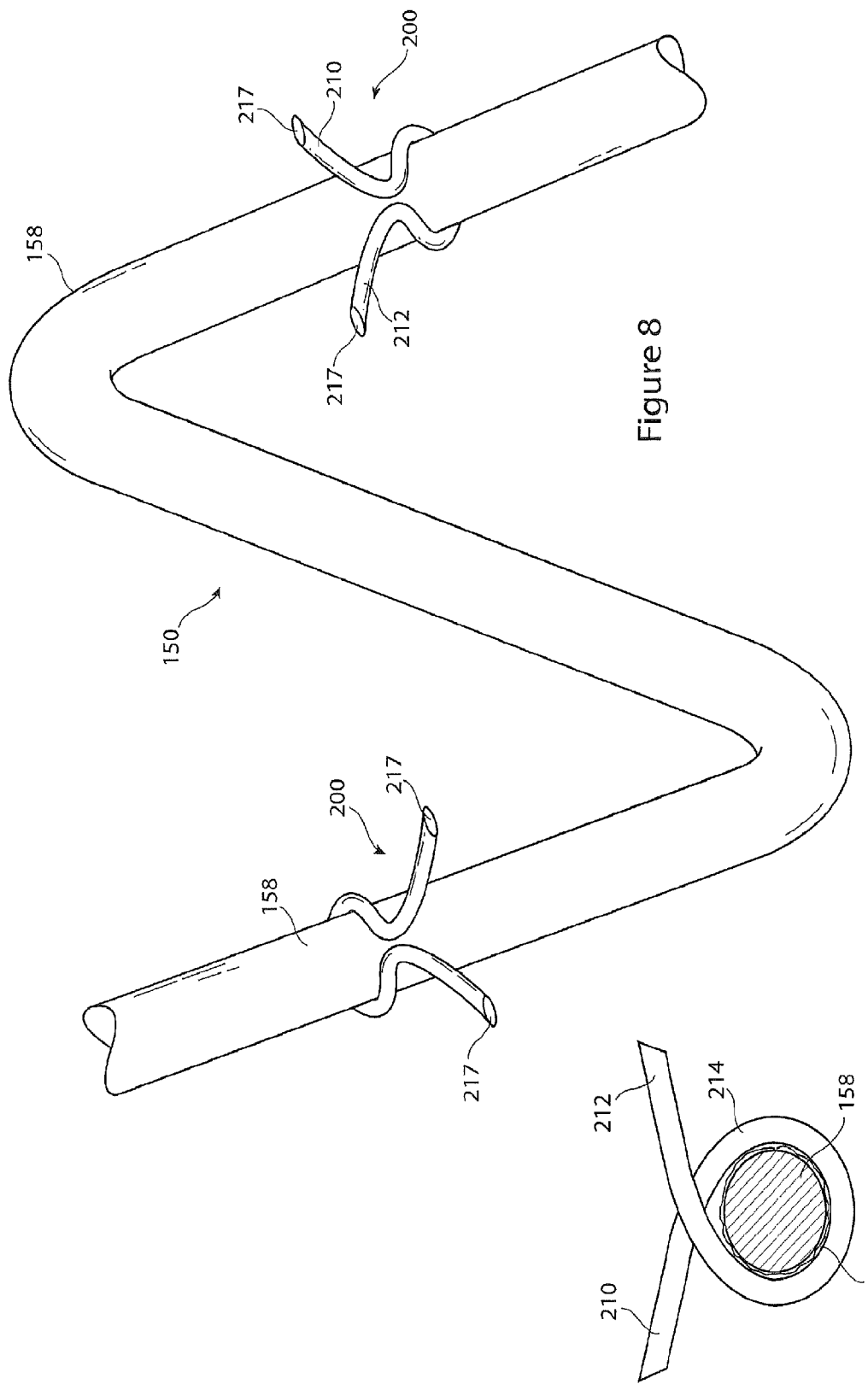

MEDICAL DEVICE DELIVERY SYSTEM AND DEPLOYMENT METHOD

RELATED APPLICATIONS

The present patent document is a §371 filing based on PCT Application Serial No. PCT/US2011/058370, filed Oct. 28, 2011 (and published as WO 2012/058582A1 on May 3, 2012), designating the United States and published in English, which claims the benefit of the filing date under 35 U.S.C. §119(e) of Provisional U.S. Patent Application Ser. No. 61/408,145, filed Oct. 29, 2010. All of the foregoing applications are hereby incorporated by reference in their entirety.

TECHNICAL FIELD

This invention relates to medical devices and, in particular, to an off-the-shelf stent-graft that is compatible with the anatomy of a majority of patients.

BACKGROUND ART

Endoluminal prostheses, such as stents and stent grafts, are used for treating damaged or diseased body lumens such as the esophagus, bile duct, and blood vessels. For example, endoluminal prostheses may be used for repairing the diseased aorta including abdominal aortic aneurysms, thoracic aortic aneurysms, and aortic arch aneurysms. The prosthesis is placed inside the body lumen and provides some or all of the functionality of the original, healthy vessel.

Endovascular aortic repair for patients with diseases (e.g. aneurysms, dissection, etc.) in the vicinity of the aortic arch is particularly challenging because the endovascular/endoluminal device, for example, a stent-graft, must be able to effectively seal off the diseased portion of the aortic arch and still allow blood flow to the branch vessels, for example, the left carotid artery, the brachiocephalic artery, and the left subclavian artery.

Access to the branch vessels is typically achieved by introducing fenestrations (apertures) in the endovascular device at locations corresponding to the location of the branch vessels, as shown in, for example, U.S. Pat. Nos. 7,144,421 and 6,524,335, the entirety of which are hereby incorporated by reference. Due to the complexity and variation amongst patients in the location of the branch vessel/aortic arch intersections, it is typically necessary to make a custom stent-graft for each individual patient. Generally, this is done by capturing the geometric data of the patient's anatomy through electromagnetic imaging (e.g. CT scans, MRI, etc.) or the like, and then manufacturing a custom, one-off stent that matches the patient's anatomy. However, this process is not cost effective and results in a long lead time. In some cases, lead time may be too long to successfully treat the patient.

DISCLOSURE OF THE INVENTION

Aortic endovascular devices, such as stent-grafts, are described which may accommodate the anatomy of a majority of patients without the need for producing custom devices. The embodiments may include any of the following aspects in various combinations and may also include any other aspect described below in the written description or in the attached drawings.

In one aspect, an aortic stent-graft may include a tubular graft extending from a proximal end to a distal end. The graft may include a proximal sealing portion and an intermediate portion, wherein a proximal end of the intermediate portion abuts the distal end of the proximal sealing portion. At least one sealing stent may be attached to the proximal sealing portion. A first fenestration window may be disposed in the intermediate portion, and may have a length determined by the equation $L_1 = 1.23 \ast D - 23$ millimeters, where $L_1$ is the length of the first fenestration window. D may be between about 24 millimeters and about 45 millimeters. D may be an average diameter of the human aorta at a midpoint between the distal coronary artery and the brachiocephalic artery.

In another aspect, the aortic stent-graft may include a second fenestration window. A proximal end of the second fenestration window may abut a distal end of the first fenestration window, and the second fenestration window may extend distally toward the distal end of the graft material. The second fenestration window may have a length determined by the equation $L_2 = 0.3 \ast D + 7$ millimeters, where $L_2$ is the length of the second fenestration window. D may be between about 24 millimeters and about 45 millimeters. D may be an average diameter of the human aorta at a midpoint between the distal coronary artery and the brachiocephalic artery.

The variable D can be a statistically derived average diameter of the aorta at a midpoint between the distal coronary artery and the brachiocephalic artery for about 80% of humans. D may be between about 24 millimeters and about 45 millimeters. D may be between about 24 millimeters and about 40 millimeters. D may be between about 30 millimeters and about 45 millimeters.

In one aspect, the first and second fenestration windows may be contiguous. In another aspect, the first and second fenestration windows may be separate and distinct windows. The proximal sealing portion may have a length of less than or equal to 55 millimeters. The proximal end of the first fenestration window may abut the distal end of the proximal sealing portion. The proximal sealing portion may be of a length such that it allows for maximal sealing contact between the stent-graft and the aorta, but does not extend past and obstruct the brachiocephalic artery when the proximal end of the sealing portion is deployed at the distal edge of the intersection between the distal coronary artery and the aorta.

The intermediate portion may have a reduced diameter as compared to the proximal and distal sealing portions. This can allow space for adjustment and alignment of tubular fenestration extensions or the like with the branch vessels in the aortic arch. The transition from the sealing portions to the intermediate portion may be tapered.

The fenestration windows may be formed from an elastic material that is easily pierced by a guidewire or the like to form a fenestration. The fenestration windows may be impervious to fluid. The fenestration windows may be formed from at least one of Dacron, Thoralon™, expanded polytetrafluoroethylene or other synthetic bio-compatible material, and naturally occurring biomaterial, such as collagen, A method of implanting a medical device in the aortic arch may include providing an aortic arch stent graft. The aortic arch stent graft may include a tubular graft extending between proximal and distal ends, with the graft comprising a proximal sealing portion and an intermediate portion. A proximal end of the intermediate portion abuts the distal end of the proximal sealing portion. At least one sealing stent may be attached to the proximal sealing portion. A first fenestration window may be disposed in the intermediate portion, the first fenestration window having a length determined by the equation $L_1=1.23*D-23$ millimeters, where $L_1$ is the length of the first fenestration window. D may be between about 24 millimeters and about 45 millimeters. D may be an average diameter of the human aorta at a midpoint between the distal coronary artery and the brachiocephalic artery.

The proximal sealing portion may be placed between the distal coronary artery and the brachiocephalic artery, thereby positioning the first fenestration window over a junction between the aorta and 1) the brachiocephalic artery and 2) the left carotid artery. The first fenestration window may be pierced at the location of the junctions between the aorta and the brachiocephalic artery and the left carotid artery to create a brachiocephalic fenestration and a left carotid fenestration, respectively.

Another method of implanting a medical device in the aortic arch may include providing an aortic arch stent graft comprising a tubular graft extending between proximal and distal ends, with the graft comprising a proximal sealing portion and an intermediate portion. A proximal end of the intermediate portion may abut the distal end of the proximal sealing portion. At least one sealing stent may be attached to the proximal sealing portion. A fenestration window is disposed in the intermediate portion. The fenestration window has a length determined by the equation $L=1.5*D-16$ millimeters, where L is the length of the fenestration window. D may be between about 24 millimeters and about 45 millimeters. D may be an average diameter of the human aorta at a midpoint between the distal coronary artery and the brachiocephalic artery.

The stent-graft may also include at least one of first, second, and third tubular extensions that extend radially outward from a wall of the fenestration window, with each tubular extension comprising a resilient support member. The first and second tubular extensions may be disposed within a proximal portion of the fenestration window. The third tubular extension may be disposed within a distal portion of the fenestration window. The proximal portion may have a length determined by the equation $L_1=1.23*D-24$ millimeters, and the distal portion may have a length determined by the equation $L_2=0.3*D+7$ millimeters, where $L_1$ is the length of the proximal portion, $L_2$ is the length of the distal portion. D may be between about 24 millimeters and about 45 millimeters. D may be the average diameter of the human aorta at the midpoint between the distal coronary artery and the brachiocephalic artery.

A human may be an adult. A human may be a child. The patient receiving treatment will generally be an adult; therefore the term 'human' used throughout the specification generally refers to an adult. However, as treatment may also be carried out on a child, the term human may refer to an adult or a child.

The proximal sealing portion may be placed between the distal coronary artery and the brachiocephalic artery, thereby positioning the fenestration window over a junction between the aorta and 1) the brachiocephalic artery, 2) the left carotid artery, and 3) the left subclavian artery for about 80% of humans. A brachiocephalic stent-graft may be advanced through the first tubular extension and into the brachiocephalic artery, a left carotid stent-graft is advanced through the second tubular extension and into the left carotid artery, and a left subclavian stent-graft is advanced through the third tubular extension and into the left subclavian artery. The foregoing paragraphs have been provided by way of general introduction, and are not intended to limit the scope of the following claims. The described embodiments will be best understood by reference to the following detailed description taken in conjunction with the accompanying drawings.

Another method of implanting a medical device in the aortic arch, comprises: providing an aortic arch stent graft comprising: a tubular graft extending between proximal and distal ends, the graft comprising a proximal sealing portion and an intermediate portion, wherein a proximal end of the intermediate portion abuts the distal end of the proximal sealing portion; at least one sealing stent attached to the proximal sealing portion; a fenestration window disposed in the intermediate portion, the fenestration window having a length determined by the equation $L=1.5*D-16$ millimeters, where L is the length of the first fenestration window; a first, second, and third tubular extension extending radially outward from a wall of the fenestration window, each tubular extension comprising a resilient support member, wherein the first and second tubular extensions are disposed within a proximal portion of the fenestration window and the third tubular extension is disposed within a distal portion of the fenestration window, wherein the proximal portion has a length determined by the equation $L_1=1.23*D-24$ millimeters, and wherein the distal portion has a length determined by the equation $L_2=0.3*D+7$ millimeters, where $L_1$ is the length of the proximal portion, $L_2$ is the length of the distal portion; placing the proximal sealing portion between the distal coronary artery and the brachiocephalic artery, thereby positioning the fenestration window over a junction between the aorta and 1) the brachiocephalic artery, 2) the left carotid artery, and 3) the left subclavian artery; advancing a brachiocephalic stent-graft through the first tubular extension and into the brachiocephalic artery; advancing a left carotid stent-graft through the second tubular extension and into the left carotid artery; and advancing a left subclavian stent-graft through the third tubular extension and into the subclavian artery. As described hereinbefore, D may be between about 24 millimeters and about 45 millimeters. D may be an average diameter of the human aorta at a midpoint between the distal coronary artery and the brachiocephalic artery.

A stent comprising at least one stent strut and an anchor member secured to the at least one strut, wherein the anchor member comprises a pair of barbs which extend in opposing directions to one another.

The anchor member may be formed from a single wire. The single wire may be bent around the peripheral surface of the strut. The portion of the wire around the peripheral surface of the strut may be an attachment portion. The attachment portion may wrap around greater than 180 degrees around the strut. This may ensure a secure connection thereto.

The barbs may form an angle therebetween of about 140 to about 160 degrees. The anchor member may be rigidly attached to the stent by, for example, brazing, welding or adhesives. In use the barbs of the anchor member may extend substantially parallel to a longitudinal axis of a graft to which the stent is attached. The barbs may form an angle of about 10 to about 20 degrees relative to the longitudinal axis of a stent-graft to which the stent is attached.

The pair of barbs may be disposed at an apex of a bend connecting circumferentially adjacent struts of, for example, a z-stent. The barbs may alternatively be known as tines.

The stent may be a sealing stent for use in an aortic stent graft. The sealing stent comprises at least one anchor member disposed on an external side thereof, the anchor member having a pair of tines extending away from each other in opposing longitudinal directions at an angle.

The pair of tines may comprise first and second tines formed from a single contiguous wire. The wire may wrap around a strut of the sealing stent, the pair of tines thereby forming an angle therebetween of about 140 degrees to about 160 degrees.

BRIEF DESCRIPTION OF THE DRAWINGS

The embodiments may be more fully understood by reading the following description in conjunction with the drawings, in which:

FIG. 8 is a plan view of an anchor member;

FIG. 8(a) is a side partial cross-sectional view of an alternative embodiment of the anchor member of FIG. 8;

DETAILED DESCRIPTION

Throughout this specification, the terms "distal" and "distally" refer to a position, direction, or orientation that is generally away from the heart. Accordingly, the terms "proximal" and "proximally" refer to a position, direction, or orientation that is generally toward, or closer to the heart.

The terms "endoluminal device" and "endovascular device" refer to or describe objects that can be placed inside a lumen or a body passageway in a human or animal body. A lumen or a body passageway can be a naturally occurring lumen or a lumen created by surgical intervention. As used in this specification, the terms "lumen" or "body passageway" are intended to have a broad meaning and encompasses any duct (e.g., natural or iatrogenic) within the human body and can include blood vessels, respiratory ducts, gastrointestinal ducts, and the like. Thus, "endoluminal devices" or "endoluminal prosthesis" describe devices that can be placed inside one of these lumens.

The term "fenestration" refers to an opening in a structure through which fluid can pass. The term "fenestration window" refers to a portion of a device comprising a substantially fluid impenetrable covering through which a fenestration can be opened or created by piercing, cutting, tearing, or the like.

The term "stent" means any device or structure that adds rigidity, expansion force or support to a prosthesis or body lumen. A stent is used to obtain and/or maintain the patency of the body passageway while maintaining the integrity of the passageway. In addition, the stent may be used to form a fluid seal against the body lumen. The stent may be coated with a polymeric material, for example, by immersion in liquid polymer or any other method known to one of skill in the art. The stent may be located on the exterior of the device, the interior of the device, or both. A stent may be self-expanding, balloon-expandable or may have characteristics of both.

The term "graft or graft material" describes an object, device, or structure that is joined to or that is capable of being joined to a body part to enhance, repair, or replace a portion or a function of that body part. A graft by itself or with the addition of other elements, such as structural components, e.g. stents, can form an endoluminal/endovascular device commonly referred to as a "stent-graft." The graft may comprise a single material, or a composite blend of materials. These materials may be in the form of a woven fabric, a laminate, etc.

Figure 1:
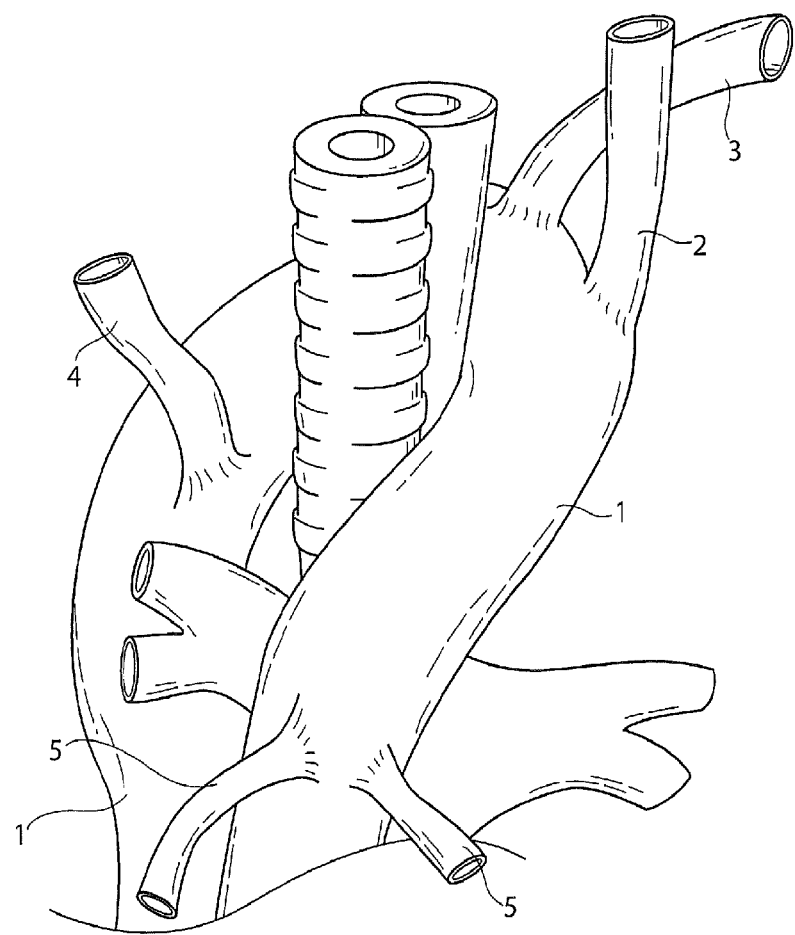
FIG. 1 is a perspective view of the aortic arch.

Referring now to the figures, FIG. 1 illustrates a typical human aortic arch including the aorta 1 and the so-called "branch vessels," including the brachiocephalic artery 2, which is also referred to as the innominate artery, the left carotid artery 3 (also referred to as the proximal carotid artery), the left subclavian artery 4 (also referred to as the distal carotid artery), and the coronary arteries 5. As shown in FIG. 1, the coronary arteries 5 are disposed closest to the heart, followed by the brachiocephalic artery 2, the left carotid artery 4, and the left subclavian artery 4. Typically, one of the two coronary arteries 5 is disposed more proximal the heart than the other. Accordingly, for the purposes of this application the coronary arteries are not referred to as "left" or "right," rather, the coronary artery disposed closest to the heart is referred to as the proximal coronary artery 5, and the coronary artery disposed furthest from the heart is referred to as the distal coronary artery 5.

Figure 2:
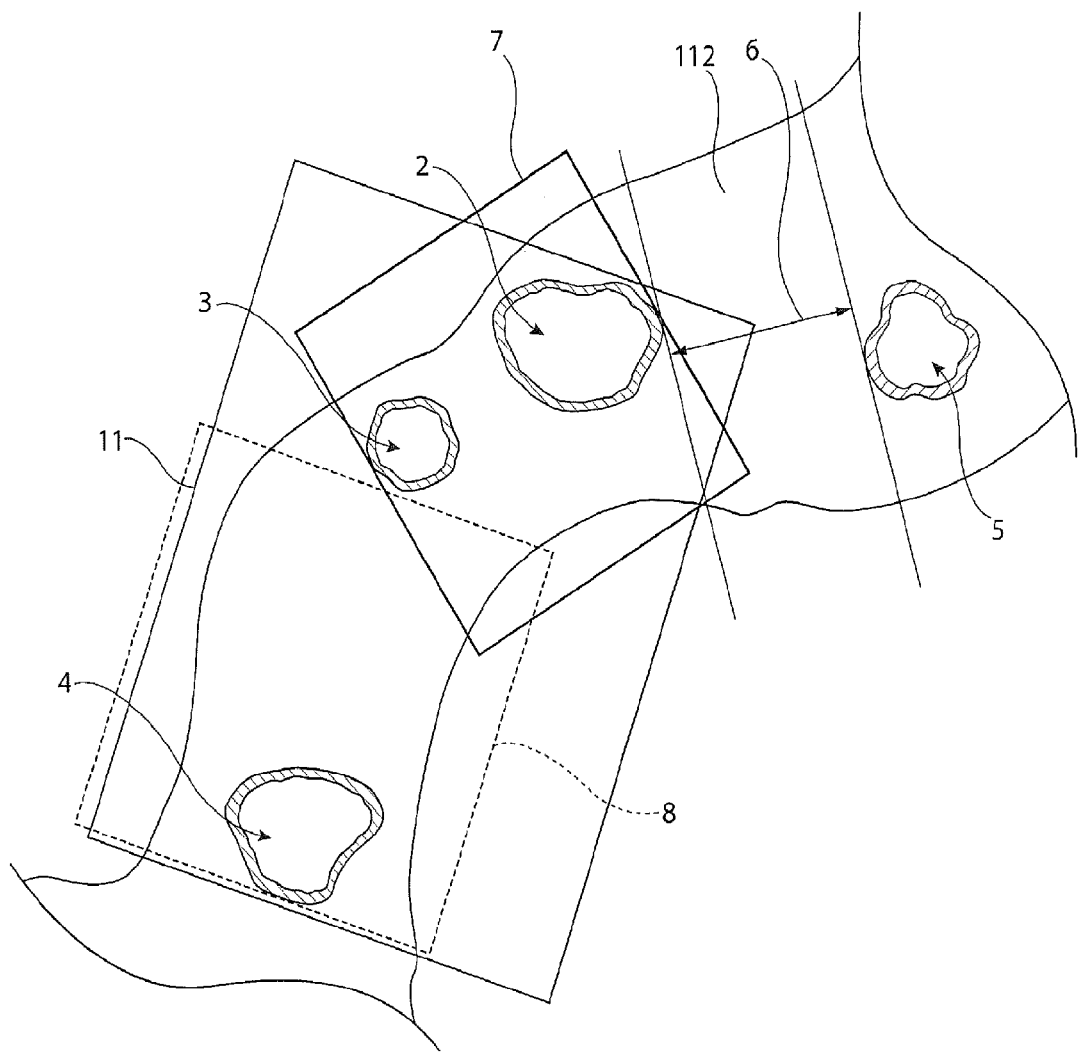
FIG. 2 is a top cross-sectional view of the aortic arch.
Figure 3:
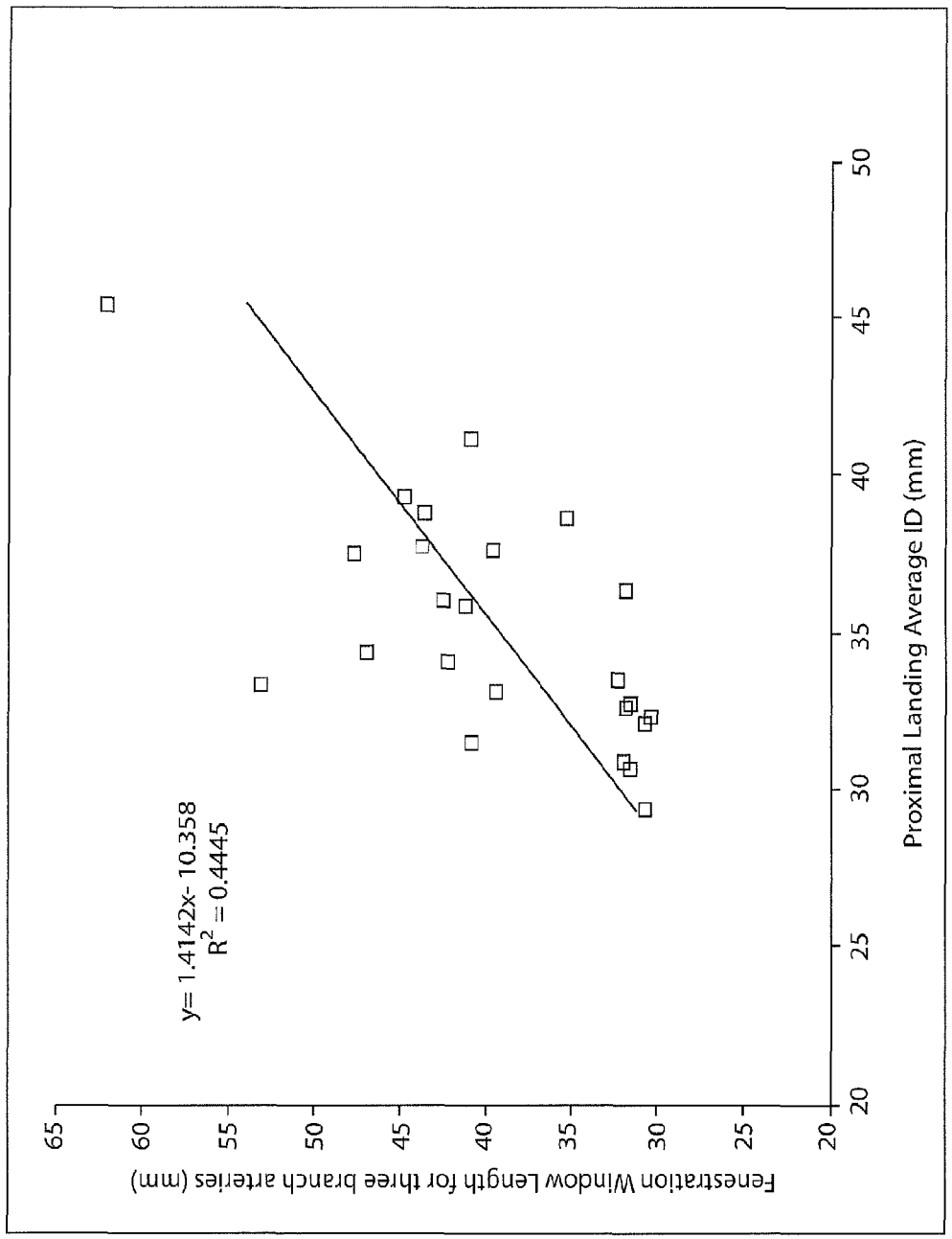
FIG. 3 is a graphical representation of the data in Tables 1-6 illustrating a novel relationship derived between the length of a fenestration window for three branch vessels and an average diameter of the aorta at a proximal landing zone.
Figure 4:
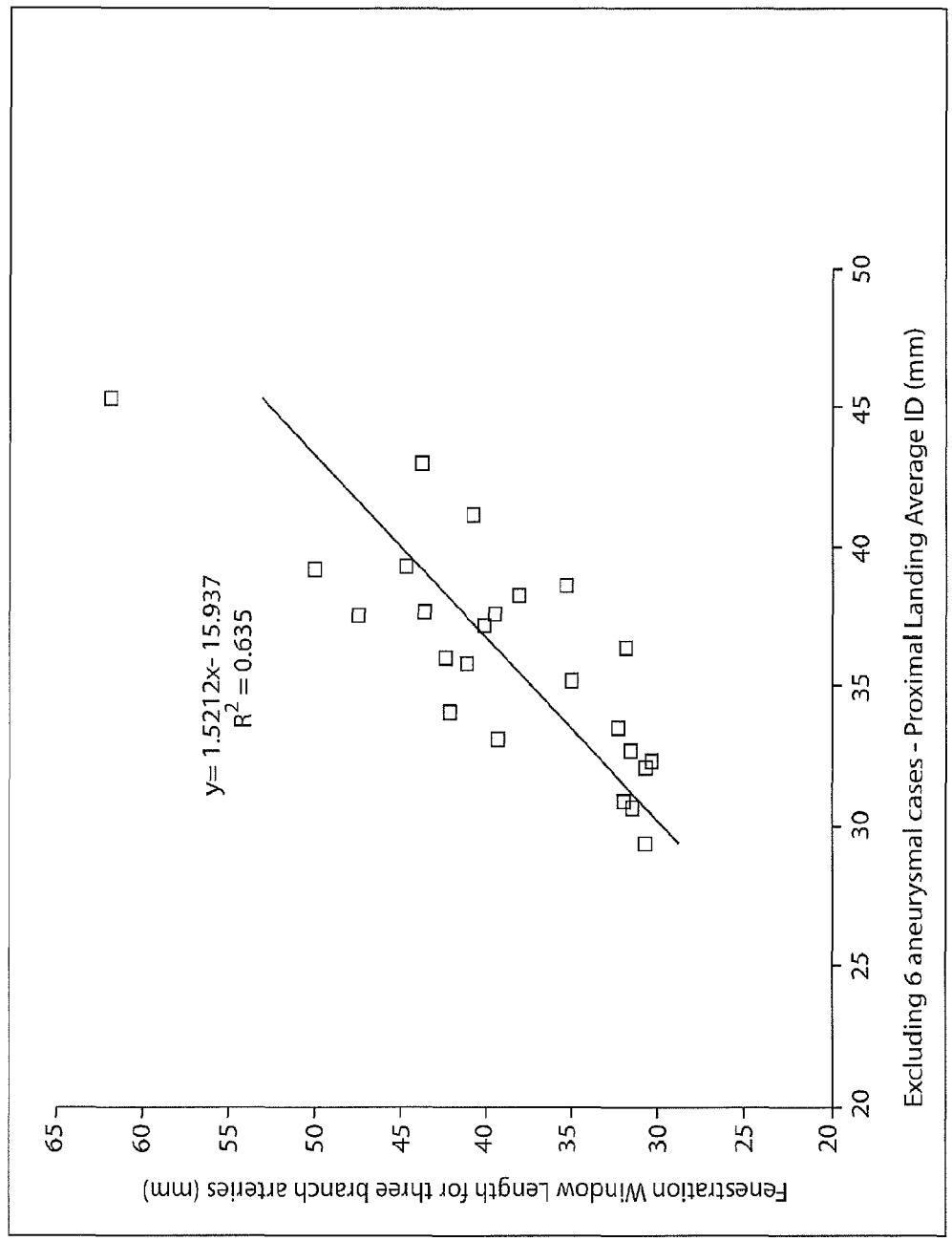
FIG. 4 is a graphical representation of the data in Tables 1-6 illustrating a novel relationship derived between the length of a fenestration window for three branch vessels and an average diameter of the aorta at a proximal landing zone excluding data for aneurismal cases.
Figure 5:
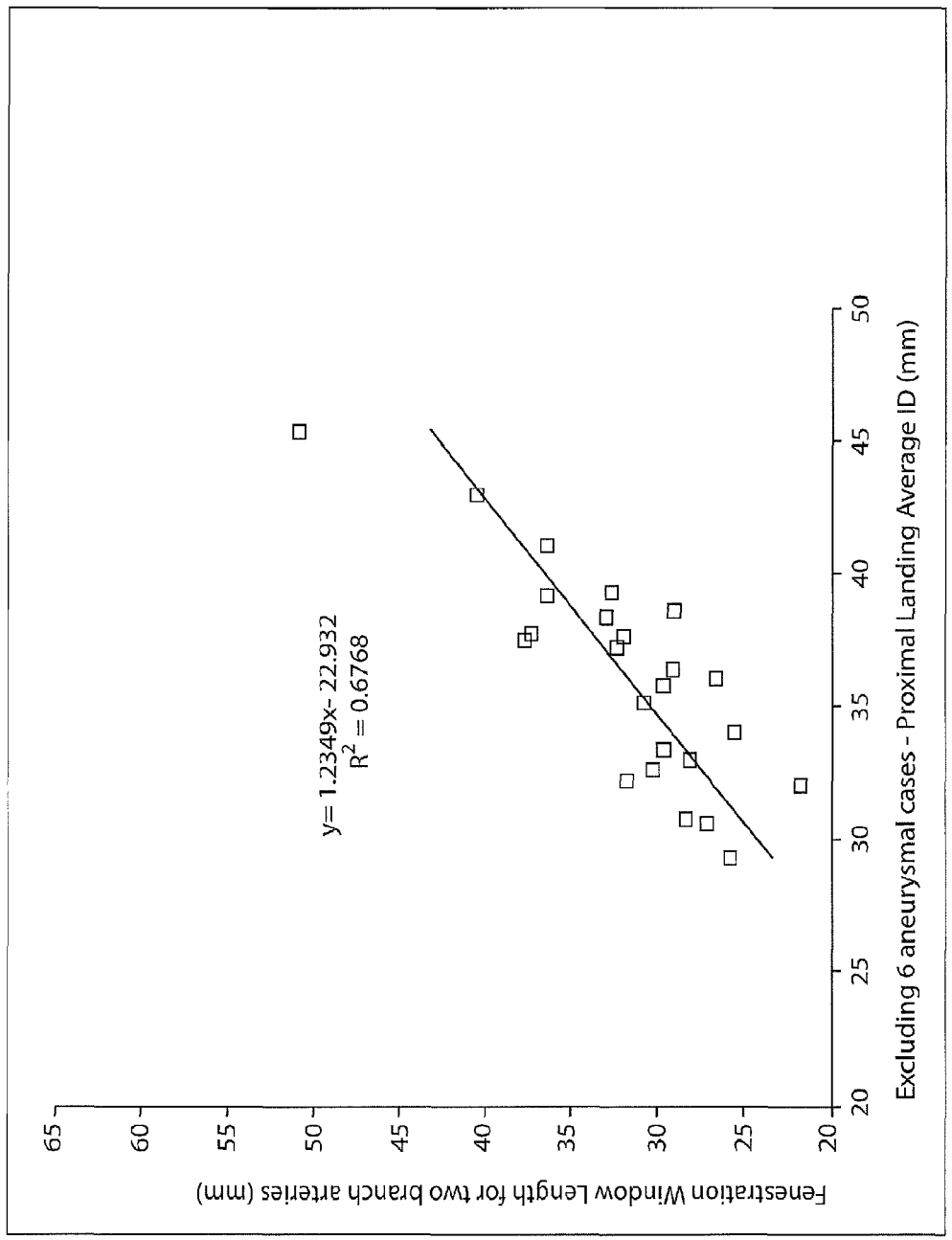
FIG. 5 is a graphical representation of the data in Tables 1-6 illustrating a novel relationship derived between the length of a fenestration window for two branch vessels and an average diameter of the aorta at a proximal landing zone excluding data for aneurismal cases.
Figure 6:
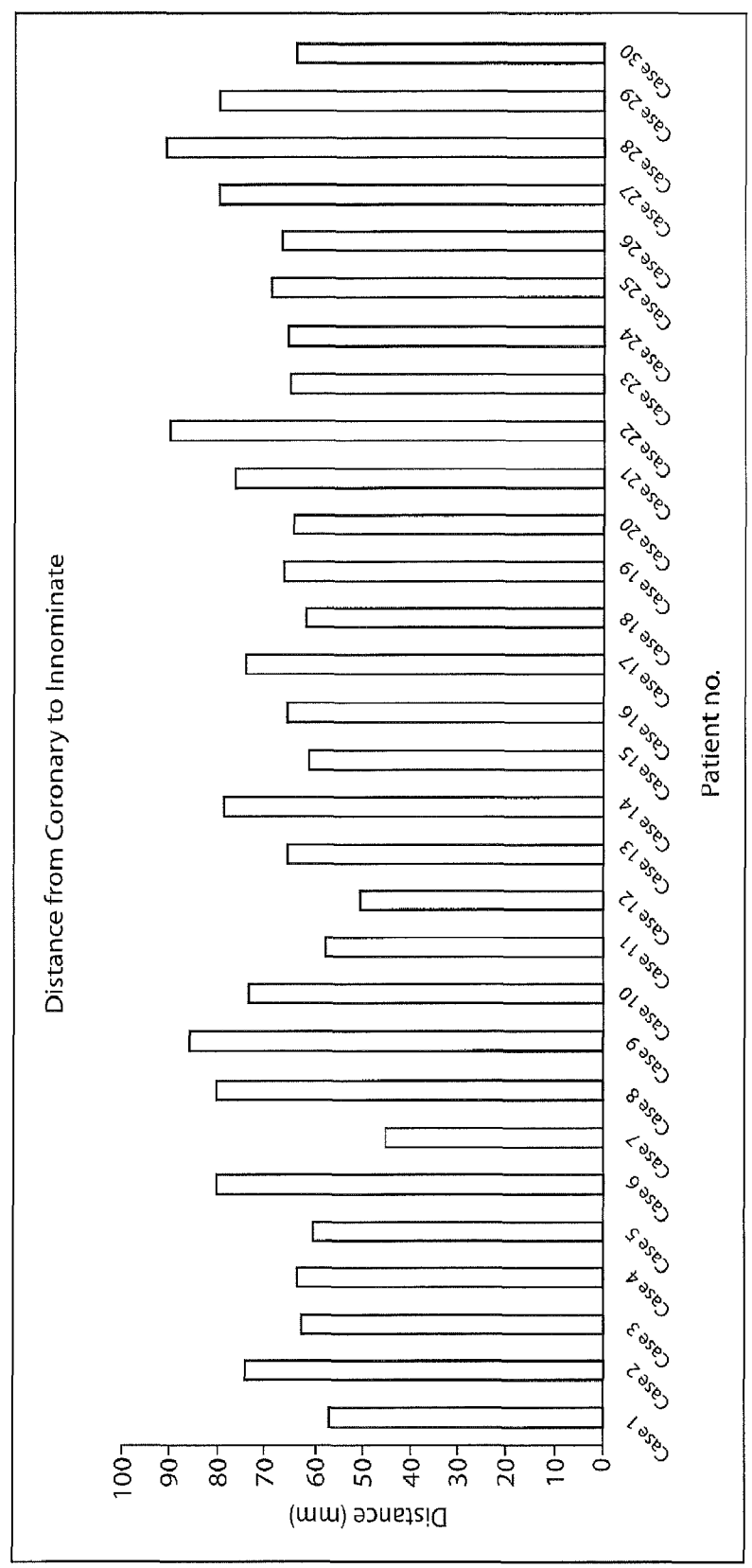
FIG. 6 is a bar graph of the average distance from the right (distal) coronary artery to a proximal edge of the brachiocephalic artery for 30 different cases.

FIG. 2 is a top view of the aortic arch showing the brachiocephalic artery 2, which is also referred to as the innominate artery, the left carotid artery 3, the left subclavian artery 4, the proximal edge of the brachiocephalic artery 2 is spaced away from the distal edge of the distal coronary artery 5 by a distance 6. Three fenestration windows 7, 8, and 11 are also shown. As shown in FIG. 2, the fenestration window 7 extends from at least the proximal edge of the brachiocephalic artery 2 to at least the distal edge of the left carotid artery 3 to form a "two-vessel" fenestration window, while the fenestration window 8 extends from the distal edge of the left carotid artery 3 to the distal edge of the left subclavian artery 4. The fenestration window 11 is configured as a "three vessel" fenestration window that extends from at least the proximal edge of the brachiocephalic artery 2, over the left carotid artery 3, and to at least the distal edge of the left subclavian artery 4. The length and placement of the fenestration windows 7, 8, and 11 are determined using the data shown in Tables 1-12 and graphically shown in FIGS. 3-6, as described in detail below, where FIG. 3 is a graphical representation of the data in Tables 1-6 illustrating a novel relationship derived between the length of a fenestration window 11 for three branch vessels and an average diameter of the aorta at a proximal landing zone between the distal coronary artery 5 and the brachiocephalic artery 2; FIG. 4 is a graphical representation of the data in Tables 1-6 illustrating a novel relationship derived between the length of a fenestration window 11 for three branch vessels and an average diameter of the aorta at a proximal landing zone excluding data for aneurismal cases; FIG. 5 is a graphical representation of the data in Tables 1-6 illustrating a novel relationship derived between the length of the fenestration window 7 for two branch vessels and an average diameter of the aorta 1 at a proximal landing zone excluding data for aneurismal cases; and FIG. 6 is a bar graph of the average distance from the distal coronary artery 5 to a proximal edge of the brachiocephalic artery 2 for 30 different cases.

FIGS. 7(*a*)-(*e*) illustrate an embodiment of an endoluminal/endovascular device or stent-graft 100 that is designed for placement within the aortic arch. As shown in FIG. 7(*a*), the stent graft 100 may include a proximal sealing portion 110, an intermediate portion 120, and a distal sealing portion 130. Each of the proximal and distal sealing portions 110, 130 includes at least one sealing stent 150 attached to an inner surface of the graft material by sutures, adhesives, laminating, or the like.

The graft may be formed from a bio-compatible material, for example and without limitation, Dacron, Thoralon™, expanded polytetrafluoroethylene or other synthetic biocompatible material. Naturally occurring biomaterial, such as collagen, may also be used. For example, specially derived collagen materials known as an extracellular matrix (ECM) material, such as small intestinal submucosa (SIS) commercially available from Cook Biotech, West Lafayette, Ind. may be used. In addition to SIS, examples of ECM's include pericardium, stomach submucosa, liver basement membrane, urinary bladder submucosa, tissue mucosa, and dura mater. SIS is particularly useful, and can be made in the fashion described in Badylak et al., U.S. Pat. No. 4,902,508; Intestinal Collagen Layer described in U.S. Pat. No. 5,733, 337 to Carr and in 17 Nature Biotechnology 1083 (November 1999). Irrespective of the origin of the material (e.g. synthetic versus naturally occurring), the material can be made thicker by making multi-laminate constructs, for example SIS constructs as described in U.S. Pat. Nos. 5,968,096; 5,955,110; 5,885,619; and 5,711,969. Other alternatives include allographs such as harvested native tissue, which is commercially available in a cryopreserved state.

As shown in, for example, FIGS. 7(*a*)-(*c*), the intermediate portion 120 may have a reduced diameter as compared to the proximal and distal sealing portions 110, 130. As shown, the transition from the sealing portions 130, 150 to the intermediate portion 120 may be tapered, i.e. going from the larger diameter of the sealing portions 110, 103 to the smaller diameter of the intermediate portion 150. In this way, when the stent-graft 100 is deployed in the aortic arch (see e.g., FIGS. 14 and 15), the sealing stents 150 provide a continual sealing force in the radially outward direction that forces the graft material against the aortic wall and creates a fluid-tight seal between the stent-graft 100 and the aorta 1 at the proximal and distal sealing portions 110, 130. However, due to the reduced expanded diameter of the intermediate portion 120, the outer surface of the intermediate portion 120 remains spaced away from the inner surface of the aorta 1 when deployed, thereby allowing space for adjustment and alignment of tubular fenestration extensions 140 (described below in greater detail) or the like with the branch vessels in the aortic arch, such as the brachiocephalic artery 2, the left carotid artery 3, and the left subclavian artery 4 (see, e.g., FIGS. 1, 2, 14, and 15).

Returning to FIGS. 7(*a*)-(*c*), 14, and 15, the intermediate portion 120 also contains one or more fenestration windows 7, 8, 11. The fenestration windows may be configured to interface with the brachiocephalic artery 2 and the left carotid artery 3 (a "two-vessel" fenestration window, e.g. fenestration window 7) or may be configured to interface with the brachiocephalic artery 2, the left carotid artery 3, and the left subclavian artery 4 (a "three-vessel" fenestration window, e.g. fenestration window 11), as shown in FIGS. 1 and 2. In the embodiment shown in FIG. 7(*b*), the fenestration windows 7 and 8 may be formed as a single, contiguous window, thereby resulting in a three-vessel fenestration window 11.

In such embodiments, the fenestration window 11 has a length 10, the determination of which will be described in detail below with regard to FIGS. 3-6 and Tables 1-12. The fenestration windows may be formed from an elastic material that is impervious to fluid and easily pierced by a guidewire or the like to form a fenestration, for example and without limitation, Thoralon™.

Figure 14:
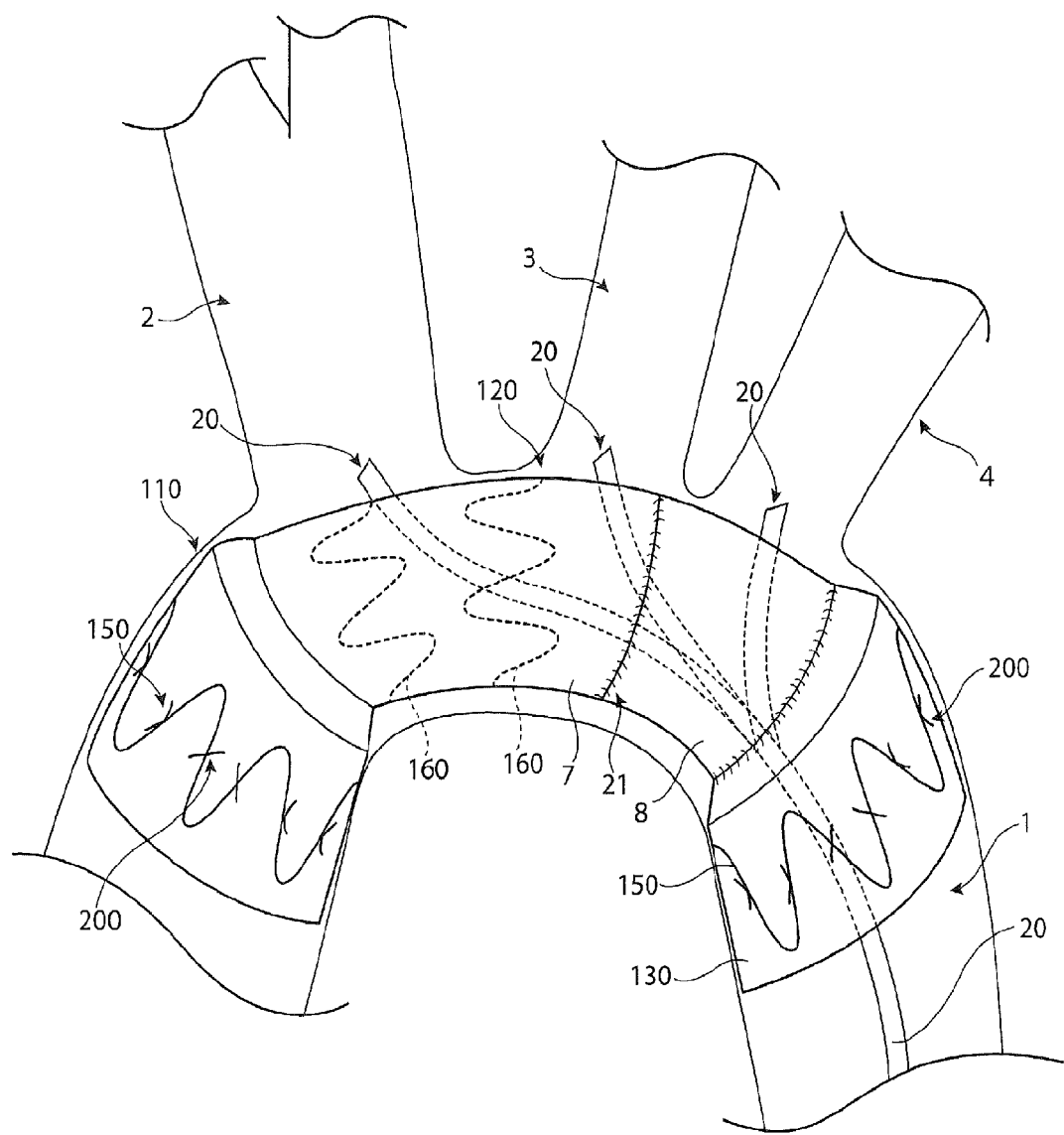
FIG. 14 is a side partial cross-sectional view of an aortic arch stent-graft deployed in an aortic arch.
Figure 15:
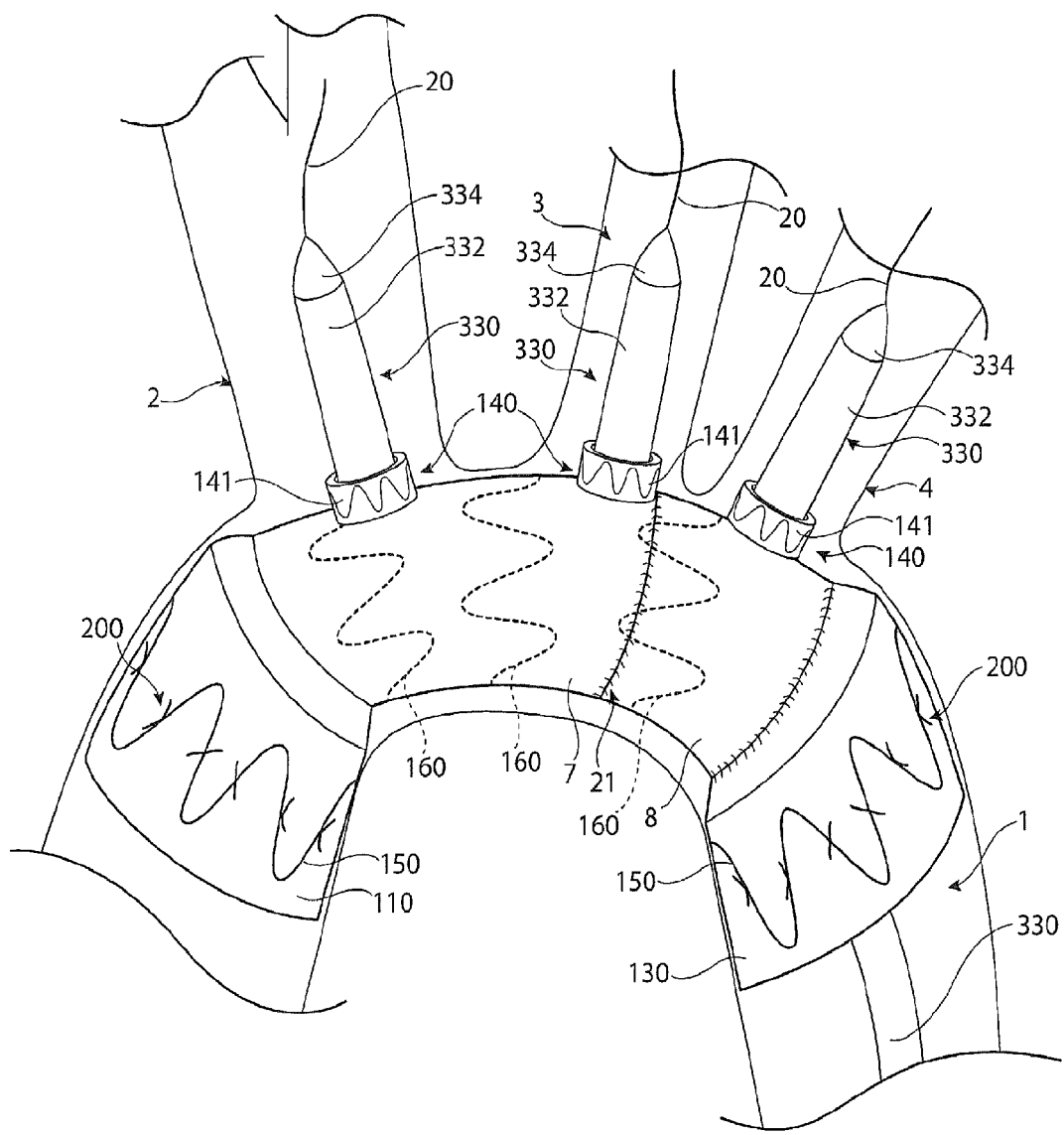
FIG. 15 is a side partial cross-sectional view of another embodiment of an aortic arch stent-graft deployed in an aortic arch.

Alternatively, a three-vessel fenestration window may be formed by attaching separate and distinct fenestration windows 7 and 8 together through sutures, adhesives or the like (using an overlapping lap-joint, etc.), as shown in FIGS. 14 and 15. A distal end of the fenestration window 7 may abut a proximal end of the fenestration window 8, and the fenestration windows may be attached to each other by sutures, adhesives (in an overlapping, lap-joint configuration), or the like. In such embodiments, the fenestration window 7 has a length 9 and the fenestration window 8 has a length 12, the determination of which will also be described in detail below with regard to FIGS. 3-6 and Tables 1-12.

Turning to FIGS. 7(*b*)-(*e*), the fenestration windows 7, 8 and 11 may extend a circumferential distance 14 roughly equal to about 180 degrees or by a circumferential distance 18 of about 270 degrees. However, it should be understood that the fenestration windows 7, 8, 11 are not limited thereto and may extend less than 180 degrees, may extend between 180 degrees and 270 degrees, or may extend 360 degrees around the circumference of the intermediate portion 120 (see FIG. 14). The fenestration windows 7, 8, 11 may be attached to the proximal and distal sealing portions 110, 130 by sutures 13 (FIG. 7(*e*)) or by adhesives (e.g. in an in an overlapping, lap-joint configuration) or the like.

As shown in FIGS. 7(*a*) and 15, the intermediate portion 120 may include one or more support stents 160 attached thereto by sutures, adhesives or the like. The support stents 160 may be attached to the inner surface or the outer surface of the intermediate portion 120. The intermediate portion 120 may also include a plurality of tubular extensions 140 attached thereto. In this case, the window may be made from the same material as the non-window portions of the graft (e.g. Dacron, Thoralon™, expanded polytetrafluoroethylene or other synthetic bio-compatible material, naturally occurring biomaterial, such as collagen, etc.). The fenestration window has an elastic property and is of a form which allows a guidewire to pierce it and form a fenestration in it. The tubular extensions 140 are configured to communicate with the branch vessels 2, 3, and 4 of FIG. 1. Specifically, the fenestration window 7 may include a brachiocephalic tubular extension 140 and a left carotid extension 140 disposed distally of the brachiocephalic tubular extension 140. The tubular extensions 140 may be disposed in a non-longitudinally overlapping manner relative to each other. They may also be circumferentially clocked from each other within about 15-30 degrees of a centerline disposed therebetween. Similarly, a left subclavian tubular extension 140 may be disposed distally of the left carotid tubular extension 140 in a non-longitudinally overlapping manner. For example, in one embodiment, the brachiocephalic tubular extension 140 may be disposed at the mean location of the proximal edge of the innominate artery plus or minus the standard deviation as detailed in any of cases 1-30 in Tables 1-12 below. Similarly, the left carotid tubular extension 140 may be disposed at the mean location of the distal edge of the left carotid artery plus or minus the standard deviation as detailed in any of cases 1-30 in Tables 1-12 below, and the left subclavian tubular extension 140 may be disposed the mean location of the distal edge of the left subclavian artery plus or minus the standard deviation as detailed in any of cases 1-30 in Tables 1-12 below. The tubular extensions 140 may be a diameter that ranges between about 8 and about 12 millimeters. The tubular extensions 140 may be spaced between 2 and 10 millimeters from each other in the longitudinal direction.

In the case where the fenestration windows 7, 8 are separate and distinct windows, the left subclavian tubular extension 140 may be disposed distally of the distal end of the two-vessel fenestration window (i.e. distal of the longitudinal junction between the fenestration window 7 and the fenestration window 8).

The tubular extensions 140 extend from a fenestration or aperture disposed in the side wall of the graft in the intermediate portion 120. The tubular extensions 140 may include a self expanding stent 141 with a bio-compatible graft material inner layer and outer layer. A ring of Nitinol or other resilient material, e.g. stainless steel or other alloy, may be disposed about the periphery of the tubular extension at the end attached to the window and/or terminal ends to provide good dimensional stability to the distal end of the tubular extensions 140. The tubular extensions 140 may be attached to the intermediate portion 120 of the graft by suturing (stitching) or the like, and generally provide a stable support and sealing surface/conduit into which another stent-graft may be inserted through and subsequently connected to form a fluid sealed structure extending into a branch artery, e.g. the brachiocephalic 2, left carotid 3, and left subclavian 4 arteries from the aorta 1. Radiopaque markers may be provided at each end of the tubular extensions 140, with one marker disposed at the base of the tubular extension 140 and one disposed at its terminal end. The radiopaque markers assist a physician in locating the tubular extensions 140 and aligning them with the branch vessels. The radiopaque markers 23 may be formed from gold, platinum or other material having radiopaque properties.

The length 9 of the fenestration window 7, the length 12 of the fenestration window 8, and the length 10 of the fenestration window 11 have been determined using statistical analysis of the anatomic geometry of 30 different cases, the results of which are illustrated in FIGS. 3-6 and Tables 1-12 below. Initially, a determination was made to use the location of the distal edge of the distalmost coronary artery 5 at its connection to the aorta 1 as a baseline for calculation of axial/longitudinal measurements to the brachiocephalic artery 2, the left carotid artery 3, and the left subclavian artery 4 (see FIGS. 1 and 2), as well as the baseline inner diameter of the aorta 1, to which all other measurements would be compared.

As shown below in tables 1-12, the inner diameter of the aorta was measured for each patient in each case at the following locations: the point of intersection between the distalmost coronary artery and the aorta (D1); the location of the midpoint between D1 and the proximal edge of the brachiocephalic (innominate) artery (D2); the location of the proximal edge of the brachiocephalic artery (D3); the location of the distal edge of the left carotid artery (D4); and the distal edge of the left (distal) subclavian artery (D5). The axial/longitudinal distance between the intersection between the distalmost coronary artery and the aorta (D1) and each of the locations D2-D5 (the distance between D1 and D2 is shown as distance 6 in FIG. 2) was also measured. A mean inner diameter was then calculated for each of the locations D1-D5, as well as a standard deviation. Based on this data, it was determined that the strongest correlation could be established by identifying fenestration windows that provide general zones in the intermediate portion 120 of the stent-graft 100 that would accommodate a majority of patients in cases 1-30 of tables 1-12. In particular, it was determined that fenestration windows capable of accommodating either two branch vessels, e.g., the brachiocephalic artery 2 and the left carotid artery 3, such as the fenestration window 7, or three branch vessels, e.g. the brachiocephalic artery 2, the left carotid artery 3, and the left subclavian artery 4, either by creating one large window 11 or combining the two-vessel fenestration window 7 with a smaller fenestration window 8 that is configured to accommodate the varied placement of the left subclavian artery 4, were suitable for a majority of patients, for example, 80%.

TABLE 1

| Branch Vessel Locations for Cases 1-5 | | | | | |
|---|---|---|---|---|---|
| | Case 1 (Avg.) | Case 2 (Avg.) | Case 3 (Avg.) | Case 4 (Avg.) | Case 5 (Avg.) |
| Branch vessel location from baseline* (mm) | | | | | |
| Distance from distal edge of distal coronary artery to proximal edge of innominate artery (mm) | 56.92 | 74.62 | 62.99 | 63.76 | 60.68 |

TABLE 1-continued

Branch Vessel Locations for Cases 1-5

|  | Case 1 (Avg.) | Case 2 (Avg.) | Case 3 (Avg.) | Case 4 (Avg.) | Case 5 (Avg.) |
| --- | --- | --- | --- | --- | --- |
| Distance from distal edge of distal coronary artery to distal edge of left carotid artery (mm) | 75.06 | 96.53 | 88.52 | 75.55 | 76.43 |
| Distance from distal edge of distal coronary artery to distal edge of left subclavian artery (mm) | 96.41 | 114.3 | 110.07 | 95.63 | 91.41 |
| Fenestration zone size (mm) | | | | | |
| Fenestration window region for innominate and left carotid artery | 18.14 | 21.91 | 25.53 | 11.79 | 15.75 |
| Fenestration window region for innominate, left carotid, and left subclavian arteries | 39.49 | 39.68 | 47.08 | 31.87 | 30.73 |
| Inner Diameter of Aorta at Proximal ** and Distal *** Landing Zones (mm) | | | | | |
| Average Inner Diameter (ID) of Proximal Landing Zone | 33.1 | 37.7 | 34.4 | 32.6 | 29.4 |
| Average Inner Diameter (ID) of Distal Landing Zone | 25.5 | 28.6 | 30.3 | 31.4 | 23.8 |
| Decrease/Increase of ID (negative number indicates ID increase) | 22.96% | 24.14% | 11.92% | 3.68% | 19.05% |
| Landing Zone ID (mm)-- Excluding aneurysmal landing zones | | | | | |
| Average Inner Diameter (ID) of Proximal Landing Zone | 33.1 | 37.7 | Excluded | Excluded | 29.4 |
| Average Inner Diameter (ID) of Distal Landing Zone | 25.5 | 38.6 | Excluded | Excluded | 23.8 |
| Decrease/Increase of ID (negative number indicates ID increase) | 22.96% | 24.14% | Excluded | Excluded | 19.05% |

*baseline determined to be the distal edge of the distal coronary artery
** Proximal Landing Zone = midpoint to innominate;
*** Distal Landing Zone = 40 mm downstream of left subclavian

TABLE 2

Branch Vessel Locations for Cases 6-10

|  | Case 6 (Avg.) | Case 7 (Avg.) | Case 8 (Avg.) | Case 9 (Avg.) | Case 10 (Avg.) |
| --- | --- | --- | --- | --- | --- |
| Branch vessel location from baseline* (mm) | | | | | |
| Distance from distal edge of distal coronary artery to proximal edge of innominate artery (mm) | 80.49 | 45.22 | 80.58 | 86.08 | 74.18 |
| Distance from distal edge of distal coronary artery to distal edge of left carotid artery (mm) | 100.08 | 63.55 | 109.34 | 105.11 | 100.58 |
| Distance from distal edge of distal coronary artery to distal edge of left subclavian artery (mm) | 121.8 | 77.19 | 124.23 | 117.89 | 115.13 |
| Fenestration zone size (mm) | | | | | |
| Fenestration window region for innominate and left carotid artery | 19.59 | 18.33 | 28.76 | 19.03 | 26.4 |
| Fenestration window region for innominate, left carotid, and left subclavian arteries | 41.31 | 31.97 | 43.65 | 31.81 | 40.95 |
| Inner Diameter of Aorta at Proximal ** and Distal *** Landing Zones (mm) | | | | | |
| Average Inner Diameter (ID) of Proximal Landing Zone | 35.9 | 30.9 | 38.9 | 36.4 | 41.2 |

TABLE 2-continued

Branch Vessel Locations for Cases 6-10

|  | Case 6 (Avg.) | Case 7 (Avg.) | Case 8 (Avg.) | Case 9 (Avg.) | Case 10 (Avg.) |
| --- | --- | --- | --- | --- | --- |
| Average Inner Diameter (ID) of Distal Landing Zone | 35.8 | 21.7 | 33 | 26.2 | 38.7 |
| Decrease/Increase of ID (negative number indicates ID increase) | 0.28% | 29.77% | 15.17% | 28.02% | 6.07% |
| Landing Zone ID (mm)-- Excluding aneurysmal landing zones | | | | | |
| Average Inner Diameter (ID) of Proximal Landing Zone | 35.9 | 30.9 | Excluded | 36.4 | 41.2 |
| Average Inner Diameter (ID) of Distal Landing Zone | 35.8 | 21.7 | Excluded | 26.2 | 38.7 |
| Decrease/Increase of ID (negative number indicates ID increase) | 0.28% | 29.77% | Excluded | 28.02% | 6.07% |

*baseline determined to be the distal edge of the distal coronary artery
** Proximal Landing Zone = midpoint to innominate;
*** Distal Landing Zone = 40 mm downstream of left subclavian

TABLE 3

Branch Vessel Locations for Cases 11-15

|  | Case 11 (Avg.) | Case 12 (Avg.) | Case 13 (Avg.) | Case 14 (Avg.) | Case 15 (Avg.) |
| --- | --- | --- | --- | --- | --- |
| Branch vessel location from baseline* (mm) | | | | | |
| Distance from distal edge of distal coronary artery to proximal edge of innominate artery (mm) | 57.89 | 50.67 | 65.96 | 79.01 | 61.69 |
| Distance from distal edge of distal coronary artery to distal edge of left carotid artery (mm) | 79.51 | 71.87 | 85.61 | 100.7 | 78.79 |
| Distance from distal edge of distal coronary artery to distal edge of left subclavian artery (mm) | 88.22 | 103.78 | 98.24 | 119.94 | 93.21 |
| Fenestration zone size (mm) | | | | | |
| Fenestration window region for innominate and left carotid artery | 21.62 | 21.2 | 19.65 | 21.69 | 17.1 |
| Fenestration window region for innominate, left carotid, and left subclavian arteries | 30.33 | 53.11 | 32.28 | 40.93 | 31.52 |
| Inner Diameter of Aorta at Proximal ** and Distal *** Landing Zones (mm) | | | | | |
| Average Inner Diameter (ID) of Proximal Landing Zone | 32.3 | 33.4 | 33.5 | 31.5 | 30.7 |
| Average Inner Diameter (ID) of Distal Landing Zone | 26.4 | 46.6 | 27.4 | 35.4 | 22.8 |
| Decrease/Increase of ID (negative number indicates ID increase) | 18.27% | −39.52% | 18.21% | −12.38% | 25.73% |
| Landing Zone ID (mm)-- Excluding aneurysmal landing zones | | | | | |
| Average Inner Diameter (ID) of Proximal Landing Zone | 32.3 | Excluded | 33.5 | Excluded | 30.7 |
| Average Inner Diameter (ID) of Distal Landing Zone | 26.4 | Excluded | 27.4 | Excluded | 22.8 |
| Decrease/Increase of ID (negative number indicates ID increase) | 18.27% | Excluded | 18.21% | Excluded | 25.73% |

*baseline determined to be the distal edge of the distal coronary artery
** Proximal Landing Zone = midpoint to innominate;
*** Distal Landing Zone = 40 mm downstream of left subclavian

TABLE 4

Branch Vessel Locations for Cases 16-20

|  | Case 16 (Avg.) | Case 17 (Avg.) | Case 18 (Avg.) | Case 19 (Avg.) | Case 20 (Avg.) |
|---|---|---|---|---|---|
| **Branch vessel location from baseline* (mm)** | | | | | |
| Distance from distal edge of distal coronary artery to proximal edge of innominate artery (mm) | 66.29 | 74.85 | 62 | 66.86 | 64.67 |
| Distance from distal edge of distal coronary artery to distal edge of left carotid artery (mm) | 93.66 | 97.47 | 73.76 | 83.51 | 84.9 |
| Distance from distal edge of distal coronary artery to distal edge of left subclavian artery (mm) | 110.08 | 119.69 | 92.76 | 109.43 | 96.28 |
| Fenestration zone size (mm) | | | | | |
| Fenestration window region for innominate and left carotid artery | 27.37 | 22.62 | 11.76 | 16.65 | 20.23 |
| Fenestration window region for innominate, left carotid, and left subclavian arteries | 43.79 | 44.84 | 30.73 | 42.57 | 31.61 |
| **Inner Diameter of Aorta at Proximal ** and Distal *** Landing Zones (mm)** | | | | | |
| Average Inner Diameter (ID) of Proximal Landing Zone | 37.8 | 39.4 | 32.1 | 36.1 | 32.7 |
| Average Inner Diameter (ID) of Distal Landing Zone | 34.3 | 32 | 31.2 | 32.6 | 30.4 |
| Decrease/Increase of ID (negative number indicates ID increase) | 9.26% | 18.78% | 2.80% | 9.70% | 7.03% |
| Landing Zone ID (mm)-- Excluding aneurysmal landing zones | | | | | |
| Average Inner Diameter (ID) of Proximal Landing Zone | 37.8 | 39.4 | 32.1 | 36.1 | 32.7 |
| Average Inner Diameter (ID) of Distal Landing Zone | 34.3 | 32 | 31.2 | 32.6 | 30.4 |
| Decrease/Increase of ID (negative number indicates ID increase) | 9.26% | 18.78% | 2.80% | 9.70% | 7.03% |

*baseline determined to be the distal edge of the distal coronary artery
** Proximal Landing Zone = midpoint to innominate;
*** Distal Landing Zone = 40 mm downstream of left subclavian

TABLE 5

Branch Vessel Locations for Cases 21-25

|  | Case 21 (Avg.) | Case 22 (Avg.) | Case 23 (Avg.) | Case 24 (Avg.) | Case 25 (Avg.) |
|---|---|---|---|---|---|
| **Branch vessel location from baseline* (mm)** | | | | | |
| Distance from distal edge of distal coronary artery to proximal edge of innominate artery (mm) | 77.38 | 90.53 | 65.88 | 66.67 | 69.57 |
| Distance from distal edge of distal coronary artery to distal edge of left carotid artery (mm) | 92.91 | 131.51 | 84.9 | 94.32 | 91.80 |
| Distance from distal edge of distal coronary artery to distal edge of left subclavian artery (mm) | 119.72 | 152.58 | 101.22 | 114.34 | 109.81 |
| Fenestration zone size (mm) | | | | | |
| Fenestration window region for innominate and left carotid artery | 15.53 | 40.98 | 19.02 | 27.65 | 22.23 |

TABLE 5-continued

Branch Vessel Locations for Cases 21-25

|  | Case 21 (Avg.) | Case 22 (Avg.) | Case 23 (Avg.) | Case 24 (Avg.) | Case 25 (Avg.) |
|---|---|---|---|---|---|
| Fenestration window region for innominate, left carotid, and left subclavian arteries | 42.34 | 62.05 | 35.34 | 47.67 | 40.24 |
| Inner Diameter of Aorta at Proximal ** and Distal *** Landing Zones (mm) | | | | | |
| Average Inner Diameter (ID) of Proximal Landing Zone | 34.1 | 45.5 | 38.7 | 37.6 | 37.3 |
| Average Inner Diameter (ID) of Distal Landing Zone | 31.5 | 40 | 34.5 | 38.1 | 32.3 |
| Decrease/Increase of ID (negative number indicates ID increase) | 7.62% | 12.09% | 10.85% | −1.33% | 13.40% |
| Landing Zone ID (mm)-- Excluding aneurysmal landing zones | | | | | |
| Average Inner Diameter (ID) of Proximal Landing Zone | 34.1 | 45.5 | 38.7 | 37.6 | 37.3 |
| Average Inner Diameter (ID) of Distal Landing Zone | 31.5 | 40 | 34.5 | 38.1 | 32.3 |
| Decrease/Increase of ID (negative number indicates ID increase) | 7.62% | 12.09% | 10.85% | −1.33% | 13.40% |

*baseline determined to be the distal edge of the distal coronary artery
** Proximal Landing Zone = midpoint to innominate;
*** Distal Landing Zone = 40 mm downstream of left subclavian

TABLE 6

Branch Vessel Locations for Cases 26-30
Branch vessel location from baseline* (mm)

|  | Case 26 (Avg.) | Case 27 (Avg.) | Case 28 (Avg.) | Case 29 (Avg.) | Case 30 (Avg.) | Average for Cases 1-30 | Standard Deviation Cases 1-30 |
|---|---|---|---|---|---|---|---|
| Distance from distal edge of distal coronary artery to proximal edge of innominate artery (mm) | 67.37 | 80.51 | 91.52 | 80.9 | 64.81 | 69.685 | 11.03802 |
| Distance from distal edge of distal coronary artery to distal edge of left carotid artery (mm) | 93.68 | 103.36 | 111.59 | 111.43 | 85.54 | 91.37138 | 14.801882 |
| Distance from distal edge of distal coronary artery to distal edge of left subclavian artery (mm) | 117.54 | 118.71 | 128.16 | 124.79 | 99.84 | 109.3997 | 5.412529 |
| Fenestration zone size (mm) | | | | | | | |
| Fenestration window region for innominate and left carotid artery | 26.31 | 22.85 | 20.07 | 30.53 | 20.73 | 21.70067 | 5.8655757 |
| Fenestration window region for innominate, left carotid, and left subclavian arteries | 50.17 | 38.2 | 36.64 | 43.89 | 35.03 | 39.72733 | 7.6029313 |
| Inner Diameter of Aorta at Proximal** and Distal*** Landing Zones (mm) | | | | | | | |
| Average Inner Diameter (ID) of Proximal Landing Zone | 39.3 | 38.4 | 46.1 | 43.1 | 35.2 | 36.17667 | 4.2374914 |
| Average Inner Diameter (ID) of Distal Landing Zone | 32.4 | 30.8 | 33 | 34.7 | 33.3 | 31.82333 | 5.2964974 |
| Decrease/Increase of ID (negative number indicates ID increase) | 17.56% | 19.79% | 28.42% | 19.49% | 5.40% | 12.03% | n/a |
| Landing Zone ID (mm) - Excluding aneurysmal landing zones | | | | | | | |
| Average Inner Diameter (ID) of Proximal Landing Zone | 39.3 | 38.4 | Excluded | 43.1 | 35.2 | 34.11 | 3.6573974 |
| Average Inner Diameter (ID) of Distal Landing Zone | 32.4 | 30.8 | Excluded | 34.7 | 33.3 | 27.69 | 5.4925101 |

TABLE 6-continued

Branch Vessel Locations for Cases 26-30
Branch vessel location from baseline* (mm)

| | Case 26 (Avg.) | Case 27 (Avg.) | Case 28 (Avg.) | Case 29 (Avg.) | Case 30 (Avg.) | Average for Cases 1-30 | Standard Deviation Cases 1-30 |
|---|---|---|---|---|---|---|---|
| Decrease/Increase of ID (negative number indicates ID increase) | 17.56% | 19.79% | Excluded | 19.49% | 5.40% | 18.82% | n/a |

*baseline determined to be the distal edge of the distal coronary artery
**Proximal Landing Zone = midpoint to innominate;
***Distal Landing Zone = 40 mm downstream of left subclavian

TABLE 7

Anatomic Data for Cases 1-5

| Locations | Axial length | Inner Diameter Measurements | | | | | | Mean | SD |
|---|---|---|---|---|---|---|---|---|---|
| | | Case 1 | | | | | | | |
| Baseline ID (at distal coronary) (D1) | 0 | 24.02 | 26.33 | 24.86 | 27.58 | 33.5 | 30.34 | 27.7717 | 3.5799 |
| Midpoint to innominate (D2) | 28.46 | 31.81 | 32.36 | 32.62 | 35.37 | 35.15 | 31.37 | 33.1133 | 1.7198 |
| Proximal edge innominate (D3) | 56.92 | 33.34 | 30.58 | 31.14 | 33.26 | 31.76 | 31.45 | 31.9217 | 1.1369 |
| Distal edge left carotid (D4) | 75.06 | 27.06 | 27.53 | 30.64 | 27.86 | 27.53 | 28.88 | 28.25 | 1.3202 |
| Distal edge left subclavian (D5) | 96.41 | 25.25 | 22.37 | 21.57 | 23.45 | 24.98 | 23.31 | 23.4883 | 1.4347 |
| | | Case 2 | | | | | | | |
| Baseline ID (at distal coronary) (D1) | 0 | 37.75 | 36.78 | 35.47 | 37.68 | 37.49 | 37.47 | 37.1067 | 0.8726 |
| Midpoint to innominate (D2) | 37.31 | 37.28 | 37.97 | 38.09 | 38.05 | 38.41 | 36.16 | 37.66 | 0.8234 |
| Proximal edge innominate (D3) | 74.62 | 33.96 | 35.04 | 37.88 | 35.36 | 36.94 | 36.88 | 36.01 | 1.4618 |
| Distal edge left carotid (D4) | 96.53 | 34.37 | 35.7 | 34.54 | 29.15 | 31.63 | 33.9 | 33.215 | 2.3988 |
| Distal edge left subclavian (D5) | 114.3 | 42.1 | 35.6 | 33.52 | 36 | 37.76 | 38.76 | 37.29 | 2.9749 |
| | | Case 3 | | | | | | | |
| Baseline ID (at distal coronary) (D1) | 0 | 29.21 | 32.27 | 32.07 | 32.71 | 32.73 | 29.62 | 31.435 | 1.5905 |
| Midpoint to innominate (D2) | 31.5 | 34 | 33.5 | 34.17 | 34.67 | 35.48 | 34.77 | 34.4317 | 0.6918 |
| Proximal edge innominate (D3) | 62.99 | 33.42 | 32.44 | 32.08 | 32.23 | 33.08 | 33.17 | 32.7367 | 0.5565 |
| Distal edge left carotid (D4) | 88.52 | 27.43 | 29.37 | 29.31 | 29.09 | 28.99 | 27.46 | 28.6083 | 0.9118 |
| Distal edge left subclavian (D5) | 110.07 | 32.76 | 33.46 | 26.05 | 30.43 | 32.73 | 35.26 | 31.7817 | 3.2078 |
| | | Case 4 | | | | | | | |
| Baseline ID (at distal coronary) (D1) | 0 | 27.01 | 28.36 | 27.83 | 27.79 | 25.89 | 26.91 | 27.2983 | 0.8796 |
| Midpoint to innominate (D2) | 31.88 | 33.63 | 33.12 | 32.19 | 32.65 | 32.13 | 31.99 | 32.6183 | 0.647 |
| Proximal edge innominate (D3) | 63.76 | 33.45 | 28.97 | 29.05 | 33.21 | 35.13 | | 31.962 | 2.7946 |
| Distal edge left carotid (D4) | 75.55 | 25.94 | 30.39 | 27.83 | 28.67 | 28.42 | 25.98 | 27.8717 | 1.7083 |
| Distal edge left subclavian (D5) | 95.63 | 35.67 | 38.06 | 29.24 | 35.84 | 37.67 | 27.95 | 34.0717 | 4.3671 |
| | | Case 5 | | | | | | | |
| Baseline ID (at distal coronary) (D1) | 0 | 27.43 | 29.23 | 30.51 | 26.41 | 26.92 | 27.63 | 28.0217 | 1.547 |
| Midpoint to innominate (D2) | 30.31 | 29.11 | 29.6 | 29.04 | 28.8 | 30.32 | 29.68 | 29.425 | 0.554 |
| Proximal edge innominate (D3) | 60.68 | 29.24 | 28.55 | 28.88 | 30.04 | 31.81 | 29.28 | 29.6333 | 1.1768 |
| Distal edge left carotid (D4) | 76.43 | 28.76 | 28.79 | 27.67 | 28.81 | 30.2 | 28.94 | 28.8617 | 0.8044 |
| Distal edge left subclavian (D5) | 91.41 | 43.59 | 43.87 | 41.17 | 38.16 | 35.21 | 38.73 | 40.1217 | 3.379 |

TABLE 8

Anatomic Data for Cases 6-10

| Locations | Axial length | Inner Diameter Measurements | | | | Mean | SD |
|---|---|---|---|---|---|---|---|
| | | Case 6 | | | | | |
| Baseline ID (at distal coronary) (D1) | 0 | 32.73 | 31.44 | 32.48 | 32.84 | 32.3725 | 0.6397 |
| Midpoint to innominate (D2) | 40.4 | 36.38 | 35.84 | 36 | 35.52 | 35.935 | 0.3575 |
| Proximal edge innominate (D3) | 80.49 | 36.65 | 37.3 | 38.05 | 35.28 | 36.82 | 1.1753 |

TABLE 8-continued

Anatomic Data for Cases 6-10

| Locations | Axial length | Inner Diameter Measurements | | | | | | Mean | SD |
|---|---|---|---|---|---|---|---|---|---|
| Distal edge left carotid (D4) | 100.08 | 30.4 | 31.55 | 30.92 | 29.4 | | | 30.5675 | 0.9093 |
| Distal edge left subclavian (D5) | 121.8 | 31.09 | 27.51 | 38.38 | 33.32 | | | 32.575 | 4.5502 |
| Case 7 | | | | | | | | | |
| Baseline ID (at distal coronary) (D1) | 0 | 23.07 | 23.92 | 27.02 | 28.02 | | | 25.5075 | 2.3848 |
| Midpoint to innominate (D2) | 22.61 | 31.92 | 31.06 | 29.78 | 30.69 | | | 30.8625 | 0.8867 |
| Proximal edge innominate (D3) | 45.22 | 29.57 | 28.02 | 27.48 | 28.97 | 29.55 | 29.41 | 28.8333 | 0.8832 |
| Distal edge left carotid (D4) | 63.55 | 25.8 | 25.57 | 25.31 | 24.65 | 23.72 | | 25.01 | 0.8399 |
| Distal edge left subclavian (D5) | 77.19 | 27.99 | 32.3 | 27.37 | 26.31 | 23.6 | 23.79 | 26.8933 | 3.2087 |
| Case 8 | | | | | | | | | |
| Baseline ID (at distal coronary) (D1) | 0 | 32.67 | 32.21 | 37.11 | 30.15 | | | 33.035 | 2.9293 |
| Midpoint to innominate (D2) | 40.44 | 38.61 | 39.41 | 38.52 | 38.79 | 39.38 | | 38.942 | 0.4249 |
| Proximal edge innominate (D3) | 80.58 | 39.69 | 36.01 | 34.91 | 39.23 | 36.99 | 37.13 | 37.3267 | 1.8403 |
| Distal edge left carotid (D4) | 109.34 | 38.06 | 33.19 | 31.08 | 35.49 | 35.91 | | 34.746 | 2.681 |
| Distal edge left subclavian (D5) | 124.23 | 38.09 | 32.43 | 35.6 | 36.79 | 34.73 | | 35.528 | 2.1445 |
| Case 9 | | | | | | | | | |
| Baseline ID (at distal coronary) (D1) | 0 | 31.97 | 31.5 | 32.4 | 32.36 | 30.13 | | 31.672 | 0.9353 |
| Midpoint to innominate (D2) | 43.04 | 33.96 | 37.23 | 37.2 | 36.81 | 36.58 | | 36.356 | 1.3669 |
| Proximal edge innominate (D3) | 86.08 | 32.3 | 33.13 | 31.48 | 31.33 | 32.97 | 31.13 | 32.0567 | 0.8677 |
| Distal edge left carotid (D4) | 105.11 | 24.26 | 27.27 | 22.23 | 24.38 | | | 24.535 | 2.0731 |
| Distal edge left subclavian (D5) | 117.89 | 24.64 | 22.69 | 24.77 | 23.68 | 24.26 | | 24.008 | 0.8497 |
| Case 10 | | | | | | | | | |
| Baseline ID (at distal coronary) (D1) | 0 | 39.04 | 34.76 | 33.9 | 35.6 | | | 35.825 | 2.2529 |
| Midpoint to innominate (D2) | 37.19 | 40.31 | 41.36 | 41.09 | 40.75 | 42.67 | | 41.236 | 0.8926 |
| Proximal edge innominate (D3) | 74.18 | 40.08 | 38.97 | 37.73 | 39.7 | 41.1 | | 39.516 | 1.2599 |
| Distal edge left carotid (D4) | 100.58 | 38.9 | 35.53 | 33.45 | 36.57 | | | 36.1125 | 2.2663 |
| Distal edge left subclavian (D5) | 115.13 | 35.15 | 35.67 | 35.64 | 36.18 | 35.65 | | 35.658 | 0.3644 |

TABLE 9

Anatomic Data for Cases 11-15

| Locations | Axial length | Inner Diameter Measurements | | | | | | Mean | SD |
|---|---|---|---|---|---|---|---|---|---|
| Case 11 | | | | | | | | | |
| Baseline ID (at distal coronary) (D1) | 0 | 34.18 | 35.26 | 29.67 | 30.66 | | | 32.4425 | 2.697 |
| Midpoint to innominate (D2) | 28.94 | 33.31 | 31.77 | 32.55 | 32.44 | 31.25 | | 32.264 | 0.7873 |
| Proximal edge innominate (D3) | 57.89 | 29.64 | 28.02 | 28.76 | 30.5 | 29.04 | | 29.192 | 0.9347 |
| Distal edge left carotid (D4) | 79.51 | 26.81 | 27.7 | 25.5 | 22.7 | | | 25.6775 | 2.181 |
| Distal edge left subclavian (D5) | 88.22 | 26.12 | 26.41 | 22.45 | 21.28 | 24.18 | | 24.088 | 2.2415 |
| Case 12 | | | | | | | | | |
| Baseline ID (at distal coronary) (D1) | 0 | 34.72 | 33.73 | 30.35 | 31.66 | | | 32.615 | 1.9762 |
| Midpoint to innominate (D2) | 25.34 | 33.78 | 33.72 | 32.5 | 32.79 | 34.22 | | 33.402 | 0.7248 |
| Proximal edge innominate (D3) | 50.67 | 33.97 | 34.07 | 32.11 | 33.47 | | | 33.405 | 0.9023 |
| Distal edge left carotid (D4) | 71.87 | 37.62 | 35.82 | 33.95 | 33.4 | 35.42 | | 35.242 | 1.6645 |
| Distal edge left subclavian (D5) | 103.78 | 29.63 | 33.39 | 38.12 | 35.86 | 33.33 | | 34.066 | 3.1753 |
| Case 13 | | | | | | | | | |
| Baseline ID (at distal coronary) (D1) | 0 | 27.19 | 31.93 | 31.27 | 29.9 | 27.52 | | 29.562 | 2.1468 |
| Midpoint to innominate (D2) | 32.98 | 32.77 | 34.15 | 33.36 | 33.84 | | | 33.53 | 0.6019 |
| Proximal edge innominate (D3) | 65.96 | 33.81 | 31.65 | 32.52 | 33.47 | 35.12 | 34.29 | 33.4767 | 1.243 |
| Distal edge left carotid (D4) | 85.61 | 31.37 | 31.93 | 31.41 | 32.04 | 31.61 | 31.1 | 31.5767 | 0.3573 |
| Distal edge left subclavian (D5) | 98.24 | 27.69 | 30.01 | 29.95 | 29.59 | 32.06 | 28.18 | 29.58 | 1.5495 |
| Case 14 | | | | | | | | | |
| Baseline ID (at distal coronary) (D1) | 0 | 26.65 | 26.71 | 28.08 | 28.72 | | | 27.54 | 1.0271 |
| Midpoint to innominate (D2) | 39.71 | 31.35 | 29.88 | 30.71 | 33.67 | 31.82 | | 31.486 | 1.4214 |
| Proximal edge innominate (D3) | 79.01 | 39.72 | 37.04 | 38.54 | 37.51 | 39.89 | | 38.54 | 1.2773 |

TABLE 9-continued

Anatomic Data for Cases 11-15

| Locations | Axial length | Inner Diameter Measurements | | | | | Mean | SD |
|---|---|---|---|---|---|---|---|---|
| Distal edge left carotid (D4) | 100.7 | 31.35 | 29.88 | 30.71 | 33.67 | 31.82 | 31.486 | 1.4214 |
| Distal edge left subclavian (D5) | 119.94 | 26.04 | 24.24 | 24.53 | 23.48 | 23.84 | 24.426 | 0.986 |
| Case 15 | | | | | | | | |
| Baseline ID (at distal coronary) (D1) | 0 | 27.13 | 27.66 | 25.86 | 25.81 | 26.98 | 26.688 | 0.8188 |
| Midpoint to innominate (D2) | 30.85 | 30.53 | 29.96 | 29.51 | 31.95 | 31.58 30.46 | 30.665 | 0.9359 |
| Proximal edge innominate (D3) | 61.69 | 29.76 | 27.3 | 28.75 | 28.75 | 29.12 | 28.736 | 0.9026 |
| Distal edge left carotid (D4) | 78.79 | 25.96 | 24.8 | 26.77 | 25.45 | 28.04 | 26.204 | 1.254 |
| Distal edge left subclavian (D5) | 93.21 | 21.98 | 22.36 | 23.11 | 23.11 | 21.64 | 22.44 | 0.6625 |

TABLE 10

Anatomic Data for Cases 16-20

| Locations | Axial length | Inner Diameter Measurements | | | | | Mean | SD |
|---|---|---|---|---|---|---|---|---|
| Case 16 | | | | | | | | |
| Baseline ID (at distal coronary) (D1) | 0 | 38.31 | 39.72 | 38.1 | 35.33 | 38.3 | 37.952 | 1.6025 |
| Midpoint to innominate (D2) | 33.15 | 36.84 | 36.88 | 37.3 | 38.74 | 39.02 | 37.756 | 1.0465 |
| Proximal edge innominate (D3) | 66.29 | 41.14 | 41.84 | 40 | 37.9 | | 40.22 | 1.7226 |
| Distal edge left carotid (D4) | 93.66 | 32.36 | 33.76 | 35.11 | 35.25 | 34.93 | 34.282 | 1.2257 |
| Distal edge left subclavian (D5) | 110.08 | 30.88 | 30.21 | 33.39 | 33.06 | 34.53 | 32.414 | 1.8068 |
| Case 17 | | | | | | | | |
| Baseline ID (at distal coronary) (D1) | 0 | 35.78 | 33.39 | 37.05 | 34.62 | | 35.21 | 1.5675 |
| Midpoint to innominate (D2) | 37.43 | 37.87 | 38.78 | 41.46 | 39.42 | | 39.3825 | 1.524 |
| Proximal edge innominate (D3) | 74.85 | 38.8 | 40.53 | 43.53 | 40.3 | | 40.79 | 1.9812 |
| Distal edge left carotid (D4) | 97.47 | 36.65 | 35.26 | 35.77 | 36.41 | | 36.0225 | 0.6296 |
| Distal edge left subclavian (D5) | 119.69 | 35.84 | 36.25 | 37.25 | 36.59 | | 36.4825 | 0.5965 |
| Case 18 | | | | | | | | |
| Baseline ID (at distal coronary) (D1) | 0 | 33.87 | 33.19 | 32.8 | 33.38 | | 33.31 | 0.4446 |
| Midpoint to innominate (D2) | 31 | 29.87 | 32.03 | 34.27 | 32.38 | | 32.1375 | 1.8037 |
| Proximal edge innominate (D3) | 62 | 33.7 | 35.24 | 35.84 | | | 34.9267 | 1.1039 |
| Distal edge left carotid (D4) | 73.76 | 32.6 | 34.58 | 33.76 | 31.85 | | 33.1975 | 1.2111 |
| Distal edge left subclavian (D5) | 92.73 | 32.62 | 29.31 | 30.15 | 30.4 | | 30.62 | 1.4125 |
| Case 19 | | | | | | | | |
| Baseline ID (at distal coronary) (D1) | 0 | 30.13 | 33.24 | 33.82 | 33.51 | | 32.675 | 1.7131 |
| Midpoint to innominate (D2) | 33.57 | 35.54 | 36.22 | 36.69 | 35.8 | | 36.0625 | 0.5035 |
| Proximal edge innominate (D3) | 66.86 | 35.66 | 33.94 | 36.48 | 37.31 | | 35.8475 | 1.4391 |
| Distal edge left carotid (D4) | 83.51 | 33.07 | 33.69 | 30.11 | 31.81 | | 32.17 | 1.5805 |
| Distal edge left subclavian (D5) | 109.43 | 27.08 | 29.41 | 27.67 | 24.45 | | 27.1525 | 2.0553 |
| Case 20 | | | | | | | | |
| Baseline ID (at distal coronary) (D1) | 0 | 28.15 | 28.39 | 27.05 | 30.51 | | 28.525 | 1.4462 |
| Midpoint to innominate (D2) | 32.46 | 33.34 | 33.5 | 32.28 | 31.68 | | 32.7 | 0.8692 |
| Proximal edge innominate (D3) | 64.67 | 28.93 | 31.63 | 32.87 | 31.6 | | 31.2575 | 1.6607 |
| Distal edge left carotid (D4) | 84.9 | 29.44 | 28.25 | 28.32 | 28.23 | | 28.56 | 0.5879 |
| Distal edge left subclavian (D5) | 96.28 | 28.81 | 29.36 | 26.85 | 29.17 | | 28.5475 | 1.1544 |

TABLE 11

Anatomic Data for Cases 21-25

| Locations | Axial length | Inner Diameter Measurements | | | | | Mean | SD |
|---|---|---|---|---|---|---|---|---|
| *Case 21* | | | | | | | | |
| Baseline ID (at distal coronary) (D1) | 0 | 29.41 | 30.91 | 29.96 | 30.83 | | 30.2775 | 0.7208 |
| Midpoint to innominate (D2) | 38.84 | 34.65 | 34.99 | 33.63 | 33.13 | | 34.1 | 0.8673 |
| Proximal edge innominate (D3) | 77.38 | 32.7 | 36.56 | 36.97 | 33.93 | | 35.04 | 2.061 |
| Distal edge left carotid (D4) | 92.91 | 33.02 | 33.47 | 32.66 | 32.14 | 33.36 | 32.93 | 0.5435 |
| Distal edge left subclavian (D5) | 119.72 | 29.14 | 31.74 | 31.73 | 28.52 | | 30.2825 | 1.6962 |
| *Case 22* | | | | | | | | |
| Baseline ID (at distal coronary) (D1) | 0 | 39.88 | 40.28 | 40.42 | 41.54 | | 40.53 | 0.7111 |
| Midpoint to innominate (D2) | 45.27 | 45.56 | 45.62 | 44.64 | 46.02 | | 45.46 | 0.5836 |
| Proximal edge innominate (D3) | 90.53 | 40.98 | 40.05 | 41.09 | 42.4 | | 41.13 | 0.9667 |
| Distal edge left carotid (D4) | 131.51 | 35.14 | 35.71 | 35.39 | 36.52 | | 35.69 | 0.6005 |
| Distal edge left subclavian (D5) | 152.58 | 33.45 | 34.44 | 34.87 | 33.5 | | 34.065 | 0.7038 |
| *Case 23* | | | | | | | | |
| Baseline ID (at distal coronary) (D1) | 0 | 33.57 | 29.92 | 31.17 | 32.92 | | 31.895 | 1.6616 |
| Midpoint to innominate (D2) | 32.73 | 38.75 | 36.88 | 38.9 | 40.23 | | 38.69 | 1.3778 |
| Proximal edge innominate (D3) | 65.88 | 39.03 | 36.45 | 36.48 | 37.26 | | 37.305 | 1.2096 |
| Distal edge left carotid (D4) | 84.9 | 35.8 | 32.87 | 33.91 | 39.63 | 36.49 | 35.74 | 2.6117 |
| Distal edge left subclavian (D5) | 101.22 | 35.17 | 29.19 | 28.68 | 30.69 | | 30.9325 | 2.951 |
| *Case 24* | | | | | | | | |
| Baseline ID (at distal coronary) (D1) | 0 | 26.48 | 29.95 | 31.65 | 33.63 | | 30.4275 | 3.031 |
| Midpoint to innominate (D2) | 33.36 | 36.97 | 39.21 | 37.39 | 37 | | 37.6425 | 1.0624 |
| Proximal edge innominate (D3) | 66.67 | 35.74 | 33.83 | 36.3 | 36.72 | | 35.6475 | 1.2764 |
| Distal edge left carotid (D4) | 94.32 | 31.85 | 32.34 | 32.45 | 31.95 | | 32.1475 | 0.2922 |
| Distal edge left subclavian (D5) | 114.34 | 28.7 | 30.13 | 30.08 | 29.02 | | 29.4825 | 0.7309 |
| *Case 25* | | | | | | | | |
| Baseline ID (at distal coronary) (D1) | 0 | 31.75 | 31.21 | 33.12 | 32.97 | | 32.2625 | 0.9321 |
| Midpoint to innominate (D2) | 34.90 | 36.48 | 37.34 | 37.11 | 37.63 | 37.96 | 37.304 | 0.56 |
| Proximal edge innominate (D3) | 69.57 | 36.17 | 32.65 | 34.74 | 37.82 | 36.9 | 35.656 | 2.023 |
| Distal edge left carotid (D4) | 91.80 | 28.53 | 32.71 | 28.57 | 27.47 | | 29.32 | 2.3167 |
| Distal edge left subclavian (D5) | 109.81 | 31.34 | 31.66 | 29.73 | 28.96 | 30.42 | 30.422 | 1.1171 |

TABLE 12

Anatomic Data for Cases 26-30

| Locations | Axial length | Inner Diameter Measurements | | | | | Mean | SD |
|---|---|---|---|---|---|---|---|---|
| *Case 26* | | | | | | | | |
| Baseline ID (at distal coronary) (D1) | 0 | 34.9 | 32.96 | 35.01 | 34.52 | | 34.3475 | 0.9485 |
| Midpoint to innominate (D2) | 33.68 | 37.8 | 39.4 | 40.44 | 40.12 | 38.54 | 39.26 | 1.0956 |
| Proximal edge innominate (D3) | 67.37 | 35.84 | 34.66 | 35.67 | 35.19 | 35.12 | 35.296 | 0.4697 |
| Distal edge left carotid (D4) | 93.68 | 30.56 | 31.7 | 32.37 | 31.94 | 31.3 | 31.574 | 0.6868 |
| Distal edge left subclavian (D5) | 117.54 | 30.36 | 29.25 | 31.13 | 30.06 | 29.57 | 30.074 | 0.7297 |
| *Case 27* | | | | | | | | |
| Baseline ID (at distal coronary) (D1) | 0 | 34.94 | 30.2 | 35.55 | 36.5 | | 34.2975 | 2.8061 |
| Midpoint to innominate (D2) | 40.25 | 39.48 | 36.43 | 39.66 | 37.2 | 39.21 | 38.396 | 1.4774 |
| Proximal edge innominate (D3) | 80.51 | 36.23 | 35.63 | 36.38 | 38.68 | 37.5 | 36.884 | 1.2103 |
| Distal edge left carotid (D4) | 103.36 | 34.61 | 34.25 | 34.11 | 33.91 | 34.89 | 34.354 | 0.3938 |
| Distal edge left subclavian (D5) | 118.71 | 32.94 | 35.21 | 32.88 | 32.01 | 31.93 | 32.994 | 1.3254 |
| *Case 28* | | | | | | | | |
| Baseline ID (at distal coronary) (D1) | 0 | 40.76 | 38.28 | 38.45 | 39.08 | 40.02 | 39.318 | 1.0559 |
| Midpoint to innominate (D2) | 45.78 | 47.14 | 46.16 | 46.06 | 44.91 | | 46.0675 | 0.9126 |
| Proximal edge innominate (D3) | 91.52 | 41.57 | 40.5 | 40.56 | 45.11 | 42.43 | 42.034 | 1.8947 |
| Distal edge left carotid (D4) | 111.59 | 36.88 | 36.84 | 36.46 | 34.95 | 36.58 | 36.342 | 0.7978 |
| Distal edge left subclavian (D5) | 128.16 | 34.14 | 34.24 | 34.78 | 33.05 | 32.48 | 33.738 | 0.9428 |

TABLE 12-continued

Anatomic Data for Cases 26-30

| Locations | Axial length | Inner Diameter Measurements | | | | | Mean | SD |
|---|---|---|---|---|---|---|---|---|
| Case 29 | | | | | | | | |
| Baseline ID (at distal coronary) (D1) | 0 | 37.76 | 39.67 | 38.35 | 38.96 | 37.25 | 38.398 | 0.9567 |
| Midpoint to innominate (D2) | 40.45 | 43.41 | 42.53 | 42.68 | 42.25 | 44.42 | 43.058 | 0.8737 |
| Proximal edge innominate (D3) | 80.9 | 40.91 | 42.57 | 45.06 | 44.38 | 41.74 | 42.932 | 1.7511 |
| Distal edge left carotid (D4) | 111.43 | 37.38 | 36.89 | 34.91 | 34.66 | 37.32 | 36.232 | 1.3373 |
| Distal edge left subclavian (D5) | 124.79 | 36.52 | 37.82 | 37.04 | 38.3 | 35.7 | 37.076 | 1.0314 |
| Case 30 | | | | | | | | |
| Baseline ID (at distal coronary) (D1) | 0 | 31.8 | 33.3 | 33.8 | 34.92 | | 33.455 | 1.2946 |
| Midpoint to innominate (D2) | 32.36 | 37.27 | 36.08 | 34.04 | 35.88 | 32.92 | 35.238 | 1.7363 |
| Proximal edge innominate (D3) | 64.81 | 33.09 | 32.86 | 33.9 | 35.9 | | 33.9375 | 1.3823 |
| Distal edge left carotid (D4) | 85.54 | 30.27 | 31.48 | 29.34 | 30.53 | | 30.405 | 0.8801 |
| Distal edge left subclavian (D5) | 99.84 | 30.5 | 29.92 | 29.03 | 30.5 | | 29.9875 | 0.6944 |

As shown in FIGS. 3-6, once the data was collected for each of the 30 cases, the mean locations of each of the 30 cases were plotted on a graph and a relationship was developed between the mean inner diameter of the aorta 1 and the axial distance along a central axis of the aorta 1 at each of the respective distances (D1-D5).

As a result, considering all 30 cases, the following relationship was developed for a length of a three-vessel fenestration window 11:

$$Y = 1.4142X - 10.358,$$

where Y is the length of the fenestration window 11, X is the inner diameter of the aorta 1, and 10.358 is in millimeters. The error ("$R^2$") was calculated at 0.4445.

However, as shown in FIG. 3, a number of outlier cases were identified, all of which were patients having aortic arch aneurysms. Removing the outlier aneurismal cases (cases 3, 4, 8, 12, 14, and 28) and performing the same calculations yields the graph and relationship shown in FIG. 4:

$$Y = 1.5212X - 15.937,$$

where Y is the length of the fenestration window 11, X is the inner diameter of the aorta 1, and 15.937 is in millimeters. The error ("$R^2$") was calculated at 0.635.

Using the same data with the outlier cases removed, the relationship shown in FIG. 5 was developed for the length of a two-vessel fenestration window:

$$Y = 1.2349X - 22.932,$$

where Y is the length of the fenestration window 11, X is the inner diameter of the aorta 1, and 22.932 is in millimeters. The error ("$R^2$") was calculated at 0.6768.

Figure 7A:
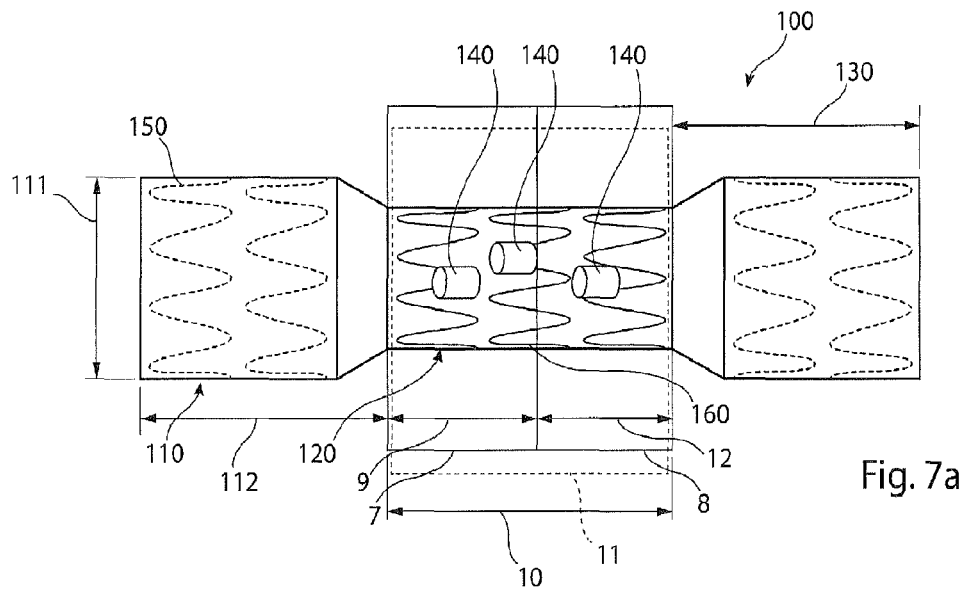
FIG. 7(a) is a top elevation view of an embodiment of an aortic arch stent-graft having two tubular fenestration extensions disposed in a first fenestration window and a third tubular fenestration extension disposed in a second fenestration window.
Figure 7B:
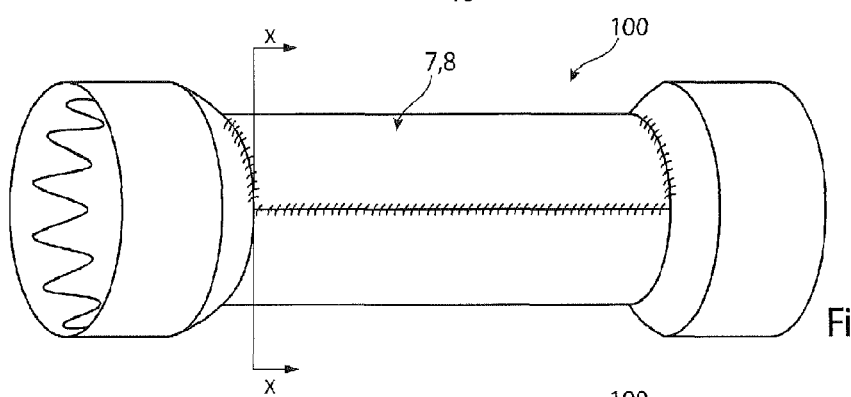
FIG. 7(b) is a plan view of an embodiment of an aortic arch stent-graft having a first and a second contiguous fenestration window configured to provide access to three branch vessels.
Figure 7C:
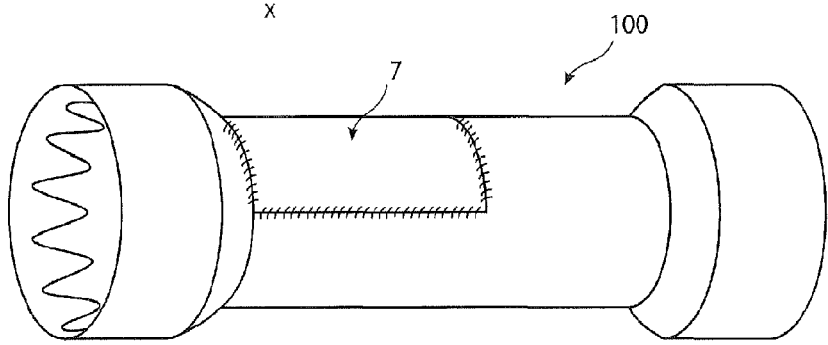
FIG. 7(c) is a plan view of an embodiment of an aortic arch stent-graft having a fenestration window configured to provide access to two branch vessels.
Figure 7D:
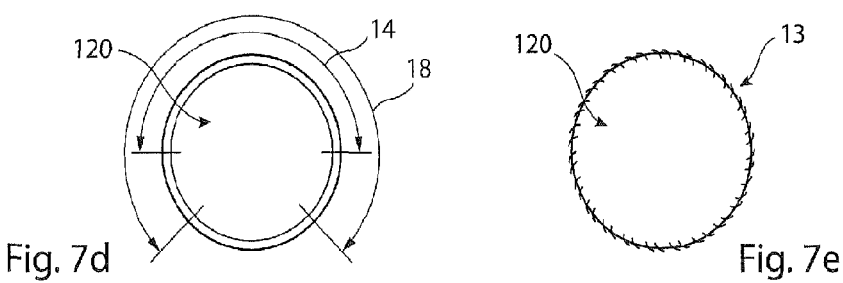
FIG. 7(d) is a side cross sectional view of the embodiment of FIG. 7(b) taken along the line X-X.
Figure 7E:
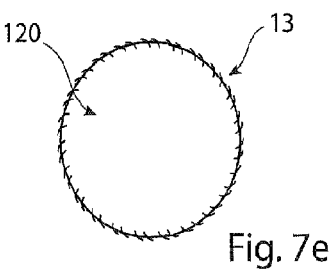
FIG. 7(e) is a side cross-sectional view of an alternative embodiment of 7(e) taken along the line X-X.

Thus, the length 9 (as shown in FIG. 7(a)) of the fenestration window 7 was determined to be governed by the relationship:

$$L_1 = 1.23*D - 23,$$

where $L_1$ is the length of the two-vessel fenestration window 7, D is a specified diameter of the aorta at the mid-point between D1 and D2, which based on the data identified in Tables 6-12 is between about 30 to about 46 millimeters. The offset 23 is in millimeters.

Similarly, the length 10 of the three-vessel fenestration window 11, was determined to be governed by the relationship:

$$L = 1.5*D - 16,$$

where L is the length of the two-vessel fenestration window 11, D is a specified diameter of the aorta at the mid-point between D1 and D2, which based on the data identified in Tables 6-12 is between about 30 to about 46 millimeters. The offset 16 is in millimeters.

Accordingly, the length 12 of the fenestration window 8 is the difference between the length of the three-vessel fenestration window 11 and the two-vessel fenestration window 7, and is governed by the relationship:

$$L_2 = 0.3*D + 7,$$

where $L_2$ is the length of the two-vessel fenestration window 8, D is a specified diameter of the aorta at the mid-point between D1 and D2, which based on the data identified in Tables 6-12 is between about 30 to about 46 millimeters. The offset 7 is in millimeters.

As shown in FIG. 6, the data for the 30 cases was also analyzed to determine a mean distance/length from the D1 position to the D2 position, in order to calculate a target length 112 (FIGS. 2 and 7(a)) for the proximal sealing portion 110 which would allow for maximal sealing contact between the stent-graft 100 and the aorta 1, but that would not extend past and obstruct the brachiocephalic artery 2 when the proximal end of the sealing portion 110 is deployed at the distal edge of the intersection between the distal coronary artery 5 and the aorta 1. This value was determined to be about 55 millimeters. It was also observed that the relative circumferential displacement of the great vessels (the brachiocephalic artery 2, the left carotid artery 3, and the subclavian artery 4) varies little from patient to patient.

Using these relationships, it is possible to produce a set number of "off-the-shelf" aortic arch stent grafts 100 that are compatible with approximately 80% of patients by simply specifying an inner diameter of the aorta 1. For example, it is possible to produce stock stent-grafts 100 that would accommodate most patients in a cost-effective manner using four to five different diameters, such as 35 millimeters, 37.5 millimeters, 40 millimeters, 42.5 millimeters and 45 millimeters. Because these stent-grafts are be produced at relatively high volume and would be readily available, they allow physicians to treat the majority of the population in a timely and cost-effective manner (e.g. next day), thereby significantly reducing the time, cost, design limitations, and quality control issues associated with the production of one-off custom devices.

Figure 9:
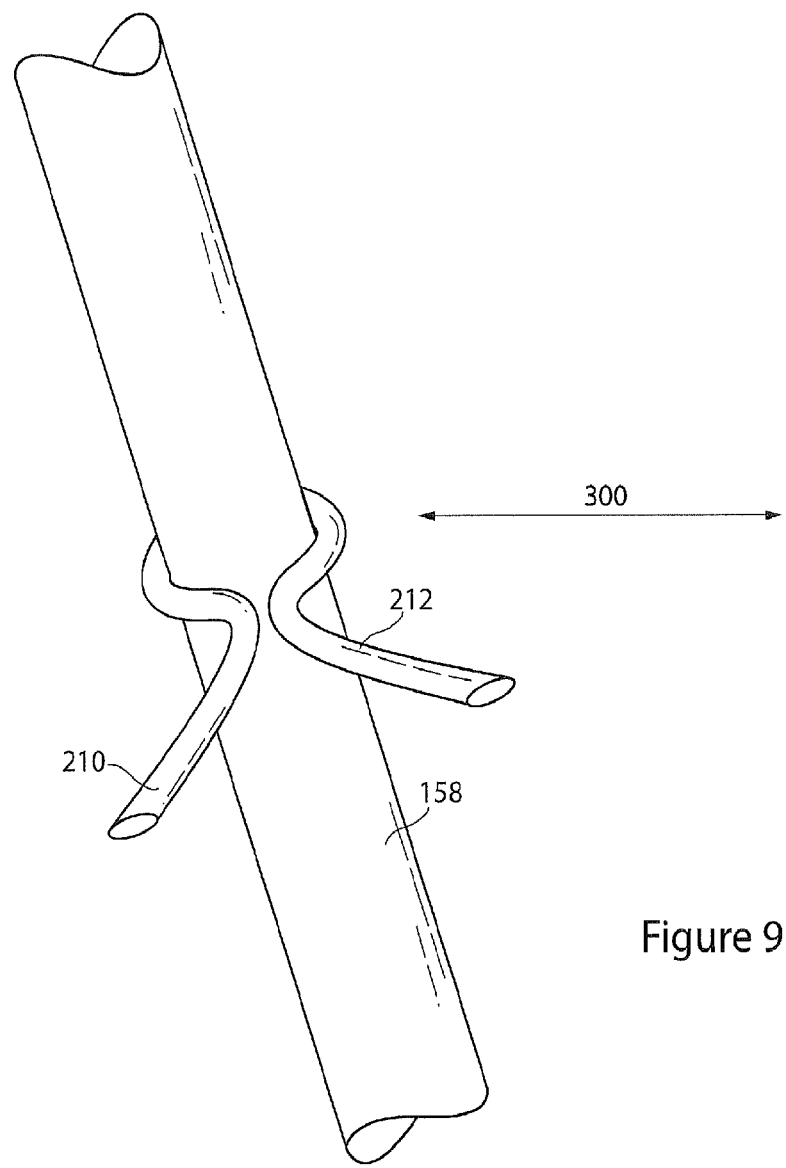
FIG. 9 is a close-up plan view of the anchor member of FIG. 8.

FIGS. 8-13 illustrate a bi-directional anchor member 200 that may be attached to the sealing stents 150 of the stent-graft 100. As shown in FIG. 8, each anchor member 200 includes a pair of tines 210, 212 that are secured to a strut 158 of the sealing stent(s) 150. Each of the tines 210, 212 includes a sharp end 217 that is designed to penetrate the wall of the vessel in which the stent-graft 100 is inserted, such as the aorta 1. In the embodiment shown in FIG. 8(*a*), the anchor member 200 may be formed from a single wire that is bent around an entire peripheral surface of the strut 158 to form an attachment portion 214 such that the tines 210 and 212 form an angle therebetween of about 140 to about 160 degrees. The anchor member 200 may be rigidly attached to the stent by brazing, welding or adhesives. As shown in FIG. 9, each tine 210, 212 may extend substantially parallel to a longitudinal axis 300 of the stent-graft 100, such that one tine 210 extends toward one end of the stent-graft 100 and the other tine 212 extends toward the opposite end of the stent-graft 100. Because the tines extend in opposite longitudinal directions, movement/migration of the stent-graft 100 is restricted/prevented in both the proximal and distal direction (with and against the flow of blood).

Figure 10:
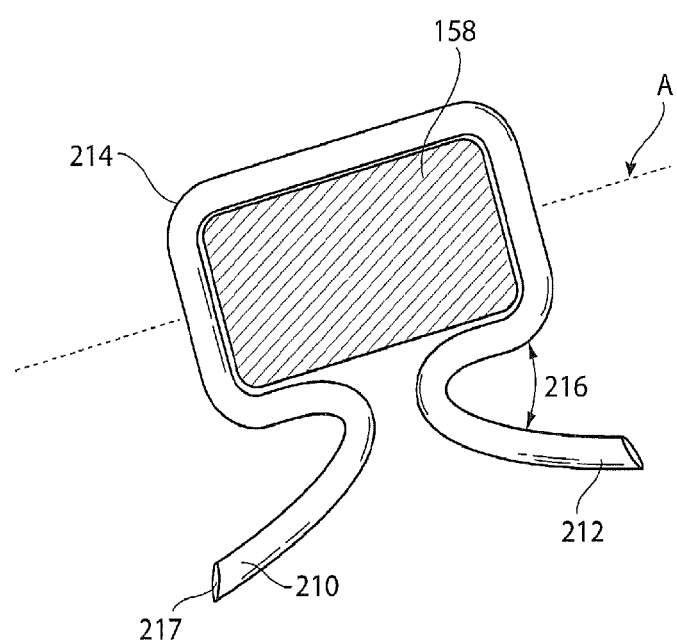
FIG. 10 is a close-up partial cross-sectional view of another embodiment of the anchor member of FIG. 8.

As shown in FIGS. 8, 9, and 10, the anchor member 200 may also be formed from a single contiguous wire to form the attachment portion 214, which is disposed between the pair of tines 210, 212. The attachment portion 214 may wrap around greater than 180 degrees around the strut 158 to ensure a secure connection thereto. One end of the attachment portion 214 is attached to the tine 210 at a first bend and the other end of the attachment portion 214 is attached to the other tine 212 at a second bend. Both the first and second bends extend away from each other in longitudinally opposite directions such that an angle is formed between the tines 210, 212 of between about 140 to about 160 degrees. In other words, the tines 210, 212 may be bent at an angle of about 10 to about 20 degrees relative to the longitudinal axis 300 of the stent-graft 100. The degree of this angle is designed to facilitate the penetration of the sharpened tip 217 into the vessel wall, while minimizing the likelihood that the tines 210, 212 will catch or damage a retention sheath of a delivery system into which the stent-graft 100 is loaded.

Figure 12:
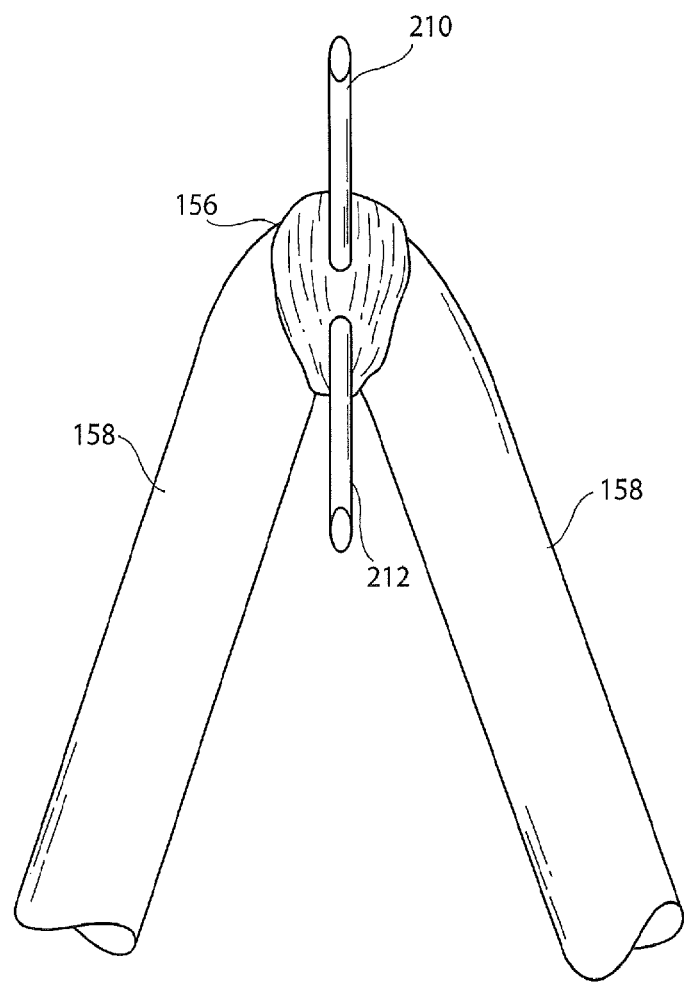
Figure 13:
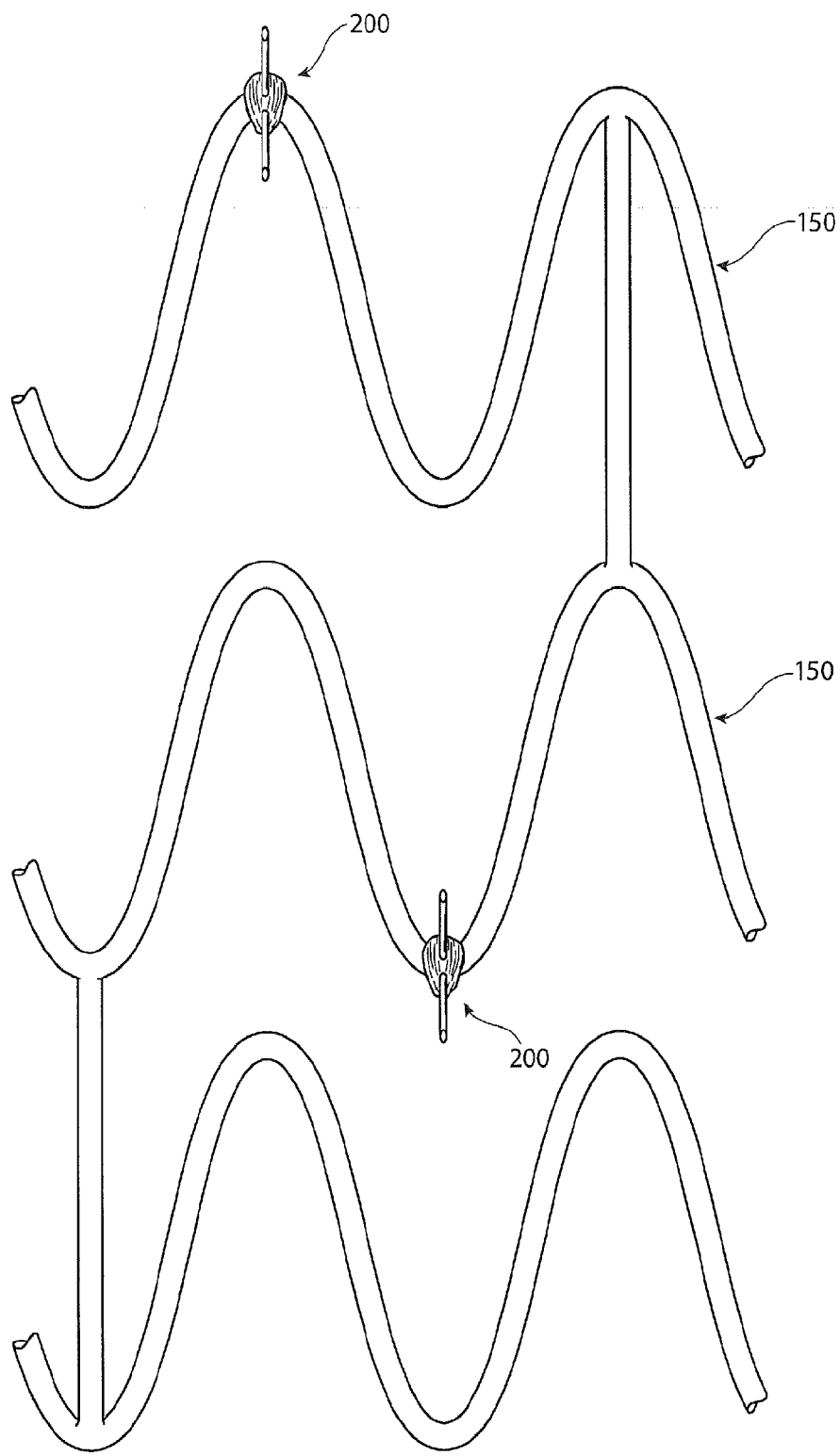

The number of anchor members 200 that are attached to the sealing stent(s) 150 may be determined based upon the diameter (and therefore the velocity of the blood) of the lumen into which the stent-graft will be inserted, e.g. the aorta. The placement of the anchor members 200 on the struts 158 may also vary depending on a number of factors, including the type of stent used, etc. As shown in FIGS. 12 and 13, the pair of tines may be disposed at an apex of a bend 156 connecting circumferentially adjacent struts 158.

Figure 11:
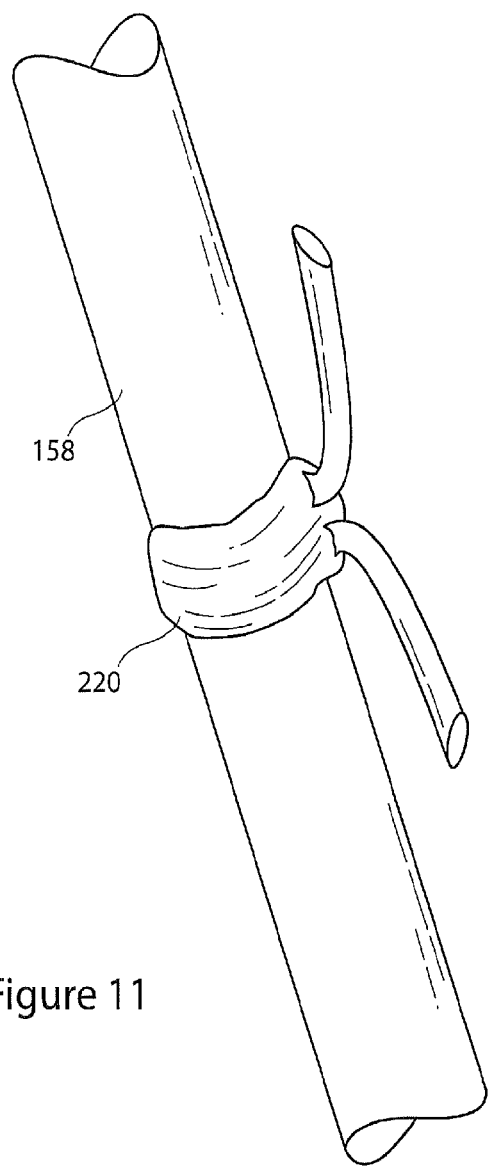
FIGS. 11-13 illustrate another embodiment of an anchor member.

FIGS. 11-13 illustrate another embodiment of the anchor member 200 in which two individual tines 210, 212 are joined together by welding, brazing, or soldering. In this embodiment, the anchor members 200 may be formed by applying solder or other bonding agent to one tine at the desired contact point with the strut 158 to form solder joint. Alternative methods for securing the individual tines 210, 212 to the strut 158 include welding, brazing, or the use of adhesives.

The materials used in the manufacture of the stent and the anchor members 200 for the stent-graft described herein may be selected from a well-known list of suitable metals. Preferred materials include those materials that can provide the desired functional characteristics with respect to mechanical load bearing, biological compatibility, modulus of elasticity, fatigue resistance, or other desired properties. In various embodiments, the stent includes a metallic material selected from stainless steel, nickel, silver, platinum, palladium, gold, titanium, tantalum, iridium, tungsten, cobalt, chromium, a nickel-titanium alloy, a superelastic nickel-titanium (NiTi) alloy sold under the tradename nitinol or inconel. The stent and tines may be manufactured from the same material so as to avoid galvanic corrosion.

The anchor members described herein may be used on any stent known to the skilled person, and are not restricted to use with the stent arrangement described herein.

FIGS. 14 and 15 illustrate the operation of different embodiments of the stent-graft 100. Exemplary delivery systems suitable for introducing and deploying the stent-graft 100 are disclosed in, for example, U.S. Pat. Pub. No. US/2003-0233140, and PCT Patent Publication No. WO 03/101518 entitled "Trigger Wires," the entirety of which are hereby incorporated by reference herein. These publications disclose release wire systems for the release of stent grafts retained on introducer devices. Additional exemplary delivery systems include those described in U.S. Pat. Pub. No. US/2004-0098079, and PCT Patent Publication No. WO 2004/028399 entitled "Thoracic Deployment Device," the entirety of which are hereby incorporated by reference herein. These publications disclose introducer devices adapted for deployment of stent grafts particularly in the thoracic arch.

Initially, the aortic arch stent graft 100 may be delivered and positioned in the aortic arch using conventional methods. For example, the stent-graft 100 may be loaded into a delivery device in a compressed, reduced diameter configuration. A retention sheath is disposed over the stent-graft 100 to hold the stent-graft 100 in the compressed configuration. The delivery system is typically inserted through an incision in, for example, the femoral artery, and advanced over a guidewire 20 to the aortic arch. The proximal end of the stent graft is advanced to a position at or near the distal edge of the junction between the distal coronary artery 5 and the aorta 1 using radiopaque markers disposed on the stent-graft 100 that are visualized under fluoroscopy or the like. The proximal end of the stent-graft 100 is then deployed by retracting the sheath and/or removing the trigger wires of the delivery device, thereby allowing the proximal sealing portion 110 to expand and appose the aorta 1 between the distal coronary artery/aorta intersection and the brachiocephalic artery/aorta intersection. The remainder of the stent-graft 100 is then deployed, with the distal sealing portion being disposed distally of the distal edge of the left subclavian artery 4 (for at least the three-vessel embodiments).

Because the proximal sealing portion 110 has a statistically determined length of, for example 55 millimeters, proper placement of the proximal sealing portion 110 results in alignment of the fenestration window 7 with both the brachiocephalic 2 and left carotid arteries 3 for 80% of patients. That is, the junctions between the brachiocephalic 2 and left carotid 3 arteries for 80% of patients are disposed at a position that corresponds with a portion of the fenestration window 7 when the stent-graft 110 is fully deployed. Similarly, in three-vessel embodiments, such as those depicted in FIGS. 14 and 15, the left subclavian artery 4 also aligns with a portion of the fenestration window 8 where the fenestration windows 7, 8 are separate (or the distal portion of the fenestration window 11 where the fenestration windows are contiguous).

As shown in FIG. 14, in embodiments where no tubular extensions 140 are employed, once the stent-graft is fully deployed, a guidewire 20 may be advanced through the stent graft 100 and used to puncture the elastic material of the fenestration windows 7, 8, or 11 to create a fenestration at each of the brachiocephalic artery 2, the left carotid artery 3, and the left subclavian artery 4. Any other suitable means to puncture the elastic material may be employed. Note that in this embodiment, the site of branch vessel/aorta intersections may be identified using MRI, CT scan, or other visualization techniques prior to the procedure and target puncture locations can be fluoroscopically marked on the fenestration windows using contrast fluid or the like. In this way, the physician can manipulate the guidewire 20 or other puncturing device to the desired location and create the fenestrations. Once the fenestrations are created, secondary branch stent-grafts housed in delivery systems are advanced over the guidewire 20, through the distal end of the stent graft 100, and into the respective branch vessels (as shown in FIG. 15). The secondary branch stent-grafts are then deployed such that a distal end apposes a wall of the branch vessel and a proximal end contacts and apposes a wall of the fenestration, thereby creating a fluid-tight seal between the aorta and the branch vessels. Note that because the material of the fenestration windows is elastic and guidewire 20 has a relatively small diameter, the puncture aperture of created by the guidewire 20 is small in comparison to the expanded diameter of the secondary stent-grafts. Thus, when the secondary stent-grafts are deployed, the aperture (fenestration) expands (elastically and/or plastically deforms) and creates a restraining, fluid-tight seal against the outer surface of the secondary stent-grafts.

Returning to FIG. 15, in embodiments utilizing tubular extensions 140, the process is essentially the same as above, except there is no need to create the fenestrations themselves using a guidewire 20 or the like. Rather, the physician utilizes radiopaque markers disposed at the terminal ends of the tubular fenestrations 140 to visualize the placement of the tubular extensions 140 relative to the branch vessel/aorta intersections, and then move the tubular extensions 140 into proper alignment therewith. Once the tubular extensions 140 are aligned, the secondary stent-grafts are advanced into the branch vessels and deployed to create a fluid-tight seal between the aorta and the branch vessels.

While preferred embodiments have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the features described above are not necessarily the only features of the invention, and it is not necessarily expected that all of the described features will be achieved with every embodiment of the invention.

What is claimed is:

1. An aortic stent-graft comprising:
a tubular graft extending from a proximal fluid inflow end to a distal fluid outflow end and having a proximal edge, the graft comprising a proximal sealing portion and an intermediate portion distal of the proximal sealing portion, wherein a proximal end of the intermediate portion abuts a distal end of the proximal sealing portion;
at least one discrete sealing stent attached to the proximal sealing portion, wherein the at least one discrete sealing stent has a proximal end adjacent the proximal end of the tubular graft, and a distal end that terminates proximal of the intermediate portion;
a first fenestration window disposed in the intermediate portion, the first fenestration window having a length determined by the equation $L_1 = 1.23*D - 23$ millimeters, where $L_1$ is the length of the first fenestration window and D is between about 24 millimeters and about 45 millimeters,
a second fenestration window, wherein a proximal end of the second fenestration window abuts a distal end of the first fenestration window,
a first fenestration and a second fenestration formed in the first fenestration window, wherein the first and second fenestrations are longitudinally spaced from one another, and
a third fenestration formed in the second fenestration window, wherein the third fenestration is longitudinally spaced from the first and second fenestrations,
wherein each of the first, second and third fenestrations has a closed perimeter which is positioned entirely distal of the proximal edge of the tubular graft, and
wherein the first and second fenestrations are separated by a longitudinal distance greater than a longitudinal distance between the second and third fenestrations,
wherein the sealing stent is disposed proximally of each of the first, second and third fenestrations,
wherein a proximal end of the first fenestration window abuts the distal end of the proximal sealing portion, the proximal sealing portion having a length of less than or equal to 55 millimeters, and
wherein the second fenestration window extends distally toward the distal end of the tubular graft, wherein the second fenestration window has a length determined by the equation $L_2 = 0.3*D + 7$ millimeters, where $L_2$ is the length of the second fenestration window and D is between about 24 millimeters and about 45 millimeters.

2. The aortic stent graft of claim 1, wherein D is a statistically derived average diameter of the aorta at a midpoint between the distal coronary artery and the brachiocephalic artery based on clinical data.

3. The aortic stent graft of claim 1, wherein D is between about 30 millimeters and about 45 millimeters.

4. The aortic stent-graft of claim 1, wherein the first and second fenestration windows are contiguous.

5. The aortic stent-graft of claim 1, wherein the first and second fenestration window are separate and distinct windows.

6. The aortic stent of claim 1, wherein the first fenestration window comprises a first and a second tubular extension extending radially outward from a wall of the first fenestration window, each tubular extension comprising a resilient support member.

7. The aortic stent-graft of claim 1, wherein first fenestration window comprises a first and a second tubular extension extending radially outward from a wall of the first fenestration window, and wherein the second fenestration window comprises a third tubular extension extending radially outward from a wall of the second fenestration window, each tubular extension comprising a resilient support member.

8. The aortic stent-graft of claim 1, wherein the first and second fenestration windows are comprised of an elastic material.

9. The aortic stent-graft of claim 1, further comprising a plurality of support stents attached to the intermediate portion, wherein said at least one sealing stent comprises at least one anchor member disposed on an external side thereof, wherein one of the at least one anchor member having a pair of tines comprising a first tine and a second tine extending away from each other in opposing longitudinal directions at an angle.

10. The aortic stent-graft of claim 9, wherein the one of the at least one anchor members comprises a single contiguous wire wrapped around a strut of the at least one sealing stent, the single contiguous wire having two free ends, the ends comprising the first and second tines thereby fainting an angle therebetween of about 140 degrees to about 160 degrees.

11. The aortic stent-graft of claim 10, wherein the single contiguous wire comprises an attachment portion disposed between the pair of tines, the attachment portion wrapping around greater than 180 degrees around the strut, wherein a first end of the attachment portion is attached to the first tine at a first bend and a second end of the attachment portion is attached to the second tine at a second bend, the first and second bends extending away from each other in longitudinally opposite directions.

12. The aortic stent graft of claim 10, wherein the at least one anchor member is rigidly attached to the strut.

13. An aortic stent-graft comprising:
a tubular graft extending from a proximal fluid inflow end to a distal fluid outflow end, the graft comprising a proximal edge, a proximal sealing portion and an intermediate portion distal of the proximal sealing portion, wherein a proximal end of the intermediate portion abuts a distal end of the proximal sealing portion;
at least one discrete sealing stent attached to the proximal sealing portion, wherein the at least one discrete sealing stent has a proximal end adjacent the proximal edge of the tubular graft, and a distal end that terminates proximal of the intermediate portion;
a first fenestration window disposed in the intermediate portion, the first fenestration window having a length determined by the equation $L_1=1.23*D-23$ millimeters, where $L_1$ is the length of the first fenestration window and D is between about 30 millimeters and about 46 millimeters,
a second fenestration window, wherein a proximal end of the second fenestration window abuts a distal end of the first fenestration window,
a first fenestration and a second fenestration formed in the first fenestration window, wherein the first and second fenestrations are longitudinally spaced from each other, and
a third fenestration formed in the second fenestration window, wherein the third fenestration is longitudinally spaced from the first and second fenestrations,
wherein each of the first, second and third fenestrations has a closed perimeter which is positioned entirely distal of the proximal inflow end of the tubular graft and
wherein the first and second fenestrations are separated by a longitudinal distance greater than a longitudinal distance between the second and third fenestrations,
wherein the at least one discrete sealing stent is disposed proximally of each of the first, second and third fenestrations,
wherein a proximal end of the first fenestration window abuts the distal end of the proximal sealing portion, the proximal sealing portion having a length of less than or equal to 55 millimeters, and
wherein the second fenestration window extends distally toward the distal end of the tubular graft, wherein the second fenestration window has a length determined by the equation $L_2=0.3*D+7$ millimeters, where $L_2$ is the length of the second fenestration window and D is between about 30 millimeters and about 46 millimeters.

14. The aortic stent graft of claim 13, wherein D is a statistically derived average diameter of the aorta at a midpoint between the distal coronary artery and the brachiocephalic artery based on clinical data.

15. The aortic stent-graft of claim 13, wherein the first and second fenestration windows are contiguous.

16. The aortic stent-graft of claim 13, wherein the first and second fenestration window are separate and distinct windows.

* * * * *

UNITED STATES PATENT AND TRADEMARK OFFICE
CERTIFICATE OF CORRECTION

PATENT NO. : 9,788,933 B2
APPLICATION NO. : 13/881632
DATED : October 17, 2017
INVENTOR(S) : Jichao Sun et al.

Page 1 of 1

It is certified that error appears in the above-identified patent and that said Letters Patent is hereby corrected as shown below:

In the Claims

In Column 33, Claim 10, Line 6, before "an angle therebetween" replace "fainting" with --forming--.

Signed and Sealed this
Twenty-eighth Day of May, 2019

Andrei Iancu
*Director of the United States Patent and Trademark Office*